(12) United States Patent
Iizuka et al.

(10) Patent No.: US 8,042,945 B2
(45) Date of Patent: Oct. 25, 2011

(54) MULTIFOCAL INTRAOCULAR LENS SIMULATOR AND METHOD OF SIMULATING MULTIFOCAL INTRAOCULAR LENS

(75) Inventors: Takashi Iizuka, Saitama (JP); Moriyasu Kanai, Saitama (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 12/897,130

(22) Filed: Oct. 4, 2010

(65) Prior Publication Data

US 2011/0080562 A1    Apr. 7, 2011

(30) Foreign Application Priority Data

Oct. 6, 2009   (JP) .................................. 2009-232502
Jun. 2, 2010   (JP) .................................. 2010-126673
Sep. 27, 2010  (JP) .................................. 2010-214672
Sep. 27, 2010  (JP) .................................. 2010-214692

(51) Int. Cl.
*A61B 3/02*   (2006.01)
*A61B 3/00*   (2006.01)

(52) U.S. Cl. ........................................ 351/233; 351/246

(58) Field of Classification Search ........... 351/200–246, 351/161, 177; 623/6.24

See application file for complete search history.

(56) References Cited

U.S. PATENT DOCUMENTS

| | | | |
|---|---|---|---|
| 5,112,351 A | 5/1992 | Christie et al. ................. 351/161 |
| 5,225,858 A * | 7/1993 | Portney .......................... 351/161 |
| 5,326,348 A * | 7/1994 | Nordan .......................... 623/6.24 |
| 5,875,017 A | 2/1999 | Ohnuma et al. ............... 351/205 |
| 6,435,681 B2 * | 8/2002 | Portney .......................... 351/161 |
| 6,638,305 B2 * | 10/2003 | Laguette ....................... 623/6.37 |
| 7,381,221 B2 | 6/2008 | Lang et al. .................... 623/6.21 |
| 2004/0111152 A1 * | 6/2004 | Kelman ......................... 623/6.37 |
| 2006/0116764 A1 | 6/2006 | Simpson ....................... 623/6.24 |

FOREIGN PATENT DOCUMENTS

| | | |
|---|---|---|
| JP | 3195386 | 6/2001 |
| JP | 3814017 | 6/2006 |
| JP | 2007-527263 | 9/2007 |
| WO | 2005/004705 | 1/2005 |

* cited by examiner

*Primary Examiner* — Mohammed Hasan
(74) *Attorney, Agent, or Firm* — Greenblum & Bernstein, P.L.C.

(57) ABSTRACT

A multifocal intraocular lens simulator includes an optical system enabling an object to be observed therethrough, and a test lens holder which holds a prescribed test intraocular lens. The intraocular lens holder is installed at a position optically conjugate with a position at which an eye of an observer is to be placed. The present invention also teaches a method of simulating a multifocal intraocular lens.

31 Claims, 19 Drawing Sheets

Diffractive Design for Central Part with Diameter of 3.6 mm

Step Height of Peripheral Part 0.4 μm

Step Height of Central Part 1.3 μm

MULTIFOCAL INTRAOCULAR LENS SIMULATOR AND METHOD OF SIMULATING MULTIFOCAL INTRAOCULAR LENS

BACKGROUND OF THE INVENTION

1. Field of the Invention

The present invention relates to a multifocal intraocular lens simulator and a method of simulating a multifocal intraocular lens.

2. Description of the Related Art

A cataract surgery treatment, in which the crystalline lens that has developed an opacification is removed and replaced by an intraocular lens (IOL) to restore the lens's transparency, has become a common surgery treatment. On the other hand, multifocal intraocular lenses are used not only for the treatment of cataracts but also for compensating the age-related decline in accommodation ability. The multifocal intraocular lens has different refractive powers: a primary refractive power, and at least one additional refractive power which corresponds to the primary refractive power to which a differential refractive power is added. Two types of the multifocal intraocular lenses are known in the art: a refractive type, and a diffractive type. The refractive type of multifocal intraocular lens has a lens surface composed of different surface areas having different curvature radiuses, the diffractive type of multifocal intraocular lens has a diffractive structure, and either of these two types of multifocal intraocular lenses forms a plurality of light converging points (one for distance vision and another for near vision) at different positions in an optical axis direction. This lens structure makes it possible for the wearer to secure sufficient eyesight at either a light converging point for distance vision or a light converging point for near vision, thus making it possible for the wearer to carry out everyday activities without having to rely on eyeglasses.

However, at least one of the two light converging points is seen as blurred image, so that this blur becomes noise, thus becoming a cause of deterioration in visibility such as contrast, etc. For instance, the diffractive multifocal intraocular lens has a disadvantage of glare (highlight glare) tending to occur, and the refractive multifocal intraocular lens has a disadvantage of a halo (optical phenomenon) tending to occur around a light (s), especially at night time. These phenomena are due to side effects of the multifocal intraocular lens implant surgery, so that a normal (healthy) eye does not visually identify such phenomena. Accordingly, one visually recognizes such phenomena only after he or she has received multifocal intraocular lens implant surgery (namely, he or she cannot actually experience (perceive) such optical phenomena before receiving such surgery).

Japanese Patent No. 3,814,017 discloses an ocular optical system simulation apparatus. In this apparatus, an intraocular lens is placed in an optical path of an imaging optical system, an image corresponding to a retinal image is captured by an image sensor such as a CCD sensor and the image is then displayed on a display monitor. According to this apparatus, an image corresponding to a retinal image is visually exhibited via an image sensor and a display monitor, and accordingly, biological factors regarding as to what sort of image processing is performed in actual human vision cannot be reflected.

Japanese Patent Domestic Announcement No. 2007-527263 discloses an apparatus devised for the fitting process for multifocal contact lenses. This apparatus synthesizes images obtained through lenses with different diopters with an addition lens being inserted into one of two branch optical paths bifurcated at some midpoint in an optical path. Although one can actually look into this apparatus to see a synthesized image, he or she cannot actually perceive the difference between capabilities of various multifocal intraocular lenses. This is because a different optical technique is used in multi-focalization by image synthesis from that in multi-focalization of an actual intraocular lens; and therefore, the apparatus disclosed in Japanese Patent Domestic Announcement No. 2007-527263 cannot depict the difference in visibility (how one sees objects) between different pupil diameters, which is a matter that can be made evident using, e.g., a refractive type of multifocal intraocular lens.

Meanwhile, multifocal intraocular lenses produced in recent years have a basic lens structure such that the energy distribution of light quantity for distance vision and near vision varies depending on the pupil diameter, regardless as to whether the lenses are of a refractive type or a diffractive type. However, such an energy distribution varies depending on the design philosophy for the lens, so that how a multifocal intraocular lens acts on the eye depends largely on the pupil diameter. Namely, how one sees objects through a multifocal intraocular lens varies depending on the pupil diameter. Since the pupil diameter varies according to light intensity and ones mental state, it is desirable that the multifocal intraocular lens simulator be equipped with the capability of monitoring or controlling the pupil diameter when one sees through the simulator.

SUMMARY OF THE INVENTION

The present invention provides a multifocal intraocular lens simulator by which one can actually perceive and experience the effects of a multifocal intraocular lens implantation, the difference between diffractive type and refractive type multifocal intraocular lenses, and also the demerits of a multifocal intraocular lens implantation without requiring to receive multifocal intraocular lens implant surgery in order to perceive/experience such effects (i.e., before receiving multifocal intraocular lens implant surgery). The present invention also provides a method of simulating a multifocal intraocular lens which achieves the above-described effects.

In addition, the present invention provides a high-precision multifocal intraocular lens simulator designed in consideration of corneal effects due to the positive refractive power of a cornea exerting an influence upon a light bundle incident on the intraocular lens implanted in an actual eye. The present invention further provides a method of simulating a multifocal intraocular lens which achieves similar effects.

Additionally, the present invention provides a multifocal intraocular lens simulator by which one can actually perceive and experience the effects of a multifocal intraocular lens implantation, the difference between diffractive type and refractive type multifocal intraocular lenses, and also the demerits of a multifocal intraocular lens implantation without requiring to receive multifocal intraocular lens implant surgery in order to perceive/experience such effects (i.e., before receiving multifocal intraocular lens implant surgery), and moreover, by which one can also actually perceive the difference in how he or she sees objects at different pupil diameters.

The present invention has been devised based on the findings that one can actually perceive and experience the effect of a multifocal intraocular lens implantation by installing a test intraocular lens in front of an optical system that enables an object (located at a far distance or a predetermined distance away) to be observed therethrough and by having an observer observe this object through the test intraocular lens and this optical system from the rear thereof.

In addition, the present invention has been devised based on the findings that one can actually perceive and experience the effect of a multifocal intraocular lens implantation by additionally installing an optical system, which has the capability of simulating the effects of the positive refractive power of a human cornea, in front of an afocal optical system.

Additionally, the present invention has been devised based on the findings that one can evaluate a multifocal intraocular lens (and actually perceive the effect thereof) in consideration of the pupil diameter if the afocal optical system is provided in an optical path thereof with an optical path splitter (e.g., a beam splitter) for use in observation of the pupil diameter.

According to an aspect of the present invention, a multifocal intraocular lens simulator is provided, including an optical system enabling an object to be observed therethrough, and a test lens holder which holds a prescribed test intraocular lens. The intraocular lens holder is installed at a position optically conjugate with a position at which an eye of an observer is to be placed.

In an embodiment, a multifocal intraocular lens simulator is provided, including an afocal optical system, wherein a parallel light bundle that enters the afocal optical system is also substantially parallel when emerging therefrom; and a test lens holder which holds a prescribed test intraocular lens (a multifocal test lens having different refractive powers: a prescribed primary refractive power, and an additional refractive power which corresponds to the primary refractive power with a differential refractive power added thereto) and is positioned in front of the afocal optical system. An observer can observe an object from the rear of the afocal optical system through the test intraocular lens and the afocal optical system, and the intraocular lens holder is installed at a position optically conjugate with a position at which an eye of the observer is to be placed.

It is desirable for the multifocal intraocular lens simulator to include a front optical system, wherein the front optical system reduces an on-axis light bundle diameter of a light bundle that is incident on the front optical system before transmitting the light bundle toward the test intraocular lens that is held by the intraocular lens holder. The front optical system and the intraocular lens holder are positioned in front of the afocal optical system so that the observer can observe the object from the rear of the afocal optical system through the test intraocular lens and the afocal optical system. A combined angular magnification of an entire optical system that includes the front optical system and the afocal optical system is approximately 1 with the intraocular lens holder holding the test intraocular lens, and the following condition is satisfied:

$$0.77 < \phi 2/\phi 1 < 0.89$$

wherein $\phi 1$ designates the on-axis light bundle diameter of the light bundle that is incident on the front optical system, and $\phi 2$ designates an on-axis light bundle diameter of the light bundle which exits from the front optical system to be incident on the test intraocular lens.

If the value $\phi 2/\phi 1$ in the above condition is equal to or less than the lower limit (0.77), the difference in the object distance between a focusable object at a far distance and a focusable object at a near distance, which is created by the differential refractive power (i.e., the difference between the additional refractive power and the primary refractive power) of the test multifocal lens (multifocal intraocular lens), that is an optical effect thereof becomes excessively smaller than the degree of the effect of a multifocal intraocular lens of the same specifications to be actually implanted in the human eye, which makes it difficult for the observer of the simulator to perceive the difference in visibility between two different focal points (or more than two focal points). If the value $\phi 2/\phi 1$ in the above condition is equal to or greater than the upper limit (0.89), the aforementioned difference in object distance between a focusable object at a far distance and a focusable object at a near distance, which is created by the differential refractive power of the test multifocal lens, becomes excessively greater than the degree of the effect of a multifocal intraocular lens of the same specifications actually implanted in the eye, e.g., the object distance of a focusable object at a near distance becomes too small with respect to a focusable object at a far distance, which makes it difficult for the observer of the simulator to experience a simulation of the usability of an implanted multifocal intraocular lens.

It is desirable for the front optical system to include a magnifying afocal optical system with an angular magnification of approximately 1.2, and for the afocal optical system to have an angular magnification of approximately 1/1.2 (approximately 0.83). It is desirable for the multifocal intraocular lens simulator to include a rear optical system having positive refractive power which is positioned between the test intraocular lens held by the intraocular lens holder and the afocal optical system, wherein the front optical system has negative refractive power. The test intraocular lens is held in a liquid by the intraocular lens holder. A combined angular magnification of an optical system ranging from the front optical system to the rear optical system is approximately 1 with the intraocular lens holder holding the test intraocular lens in the liquid.

In an embodiment, a multifocal intraocular lens simulator is provided, by which one can also actually perceive the difference in how he or she sees objects at different pupil diameters, including an afocal optical system, wherein a parallel light bundle that enters the afocal optical system is also substantially parallel when emerging therefrom; and a test lens holder which holds a prescribed test intraocular lens (a multifocal test lens having different refractive powers: a prescribed primary refractive power, and an additional refractive power which corresponds to the primary refractive power with a differential refractive power added thereto) and is positioned in front of the afocal optical system. An observer can observe an object from the rear of the afocal optical system through the test intraocular lens and the afocal optical system, and the intraocular lens holder is installed at a position optically conjugate with a position at which an eye of the observer is to be placed. Furthermore, an optical path splitter is provided, positioned in an optical path of the afocal optical system to allow a pupil diameter of the observer to be observed through a branch optical path different from the optical path of the afocal optical system. It is possible for an ocular optical system for monitoring an observer's pupil image to be installed in a branch optical path which is branched from the optical path of the test intraocular lens by the optical path splitter. However, it is more desirable for an image sensor and an imaging lens to be positioned in the branch optical path to capture an image of said pupil.

It is desirable that an index for measurement of the pupil diameter be positioned in the optical path splitter so that the pupil diameter can be visually recognized directly.

It is desirable for a light quantity controller to be provided, positioned in an optical path extending from the test intraocular lens to the optical path splitter.

To induce the pupil to increase the diameter thereof, the quantity of light incident on the pupil only needs to be reduced by the light quantity controller. Additionally, if it is desired to obtain the reverse effect, it is not necessary to force the pupil to reduce its diameter; a diaphragm only needs to be installed in an optical path so as to limit the diameter of the light bundle incident on the pupil.

The light quantity controller can be configured from, e.g., an ND filter or a diaphragm.

It is desirable for the ND filter to be movable to change the light transmittance one of continuously and stepwise. It is desirable for the diaphragm to be an adjustable diaphragm which can vary a size of an aperture thereof.

The multifocal intraocular lens simulator according to the present invention enables an observer to perceive visibility similar to what he or she would actually perceive when wearing a multifocal intraocular lens by relaying the optical effect of a test intraocular lens to a vicinity of a crystalline lens of the observer. To achieve this simulator, a test lens holder for holding a test intraocular lens is installed at a position (pupil conjugate point) optically conjugate with the position where an eye (pupil) of the observer is to be placed, and an afocal optical system enabling a distant object to be observed therethrough is used.

The afocal optical system is of Keplerian type, in which a real image of an object is formed in the afocal optical system. Namely, although there are two types of afocal optical systems available: a Keplerian type and a Galilean type, the afocal optical system is desirably a Keplerian type that has a structure in which a real image is formed at the pupil conjugate point.

It is desirable for the multifocal intraocular lens simulator to be a binocular type having a pair of identical optical systems, each of which includes the afocal optical system, so that the observer can observe objects in a more natural manner.

It is desirable for an index to be provided in a close vicinity of the real image formed in the afocal optical system to indicate a spacial position in the close vicinity of the real image. Accommodation ability of a normal (healthy) eye is produced by variations in shape of the crystalline lens in the eye, however, if the crystalline lens is replaced by a shape-fixed intraocular lens in a cataract surgery or the like, the patient looses the accommodation ability of the eye. Hence, the eye of a patient in which the crystalline lens is replaced by a shape-fixed intraocular lens has no accommodation ability; however, the multifocal intraocular lens simulator according to the present invention is configured on the assumption that the simulator is also used by the observer having normal eyes. Since a normal eye has accommodation ability, the optical effect of a test intraocular lens (a test multifocal lens or a test piece optically equivalent thereto) and the accommodation action of the normal eye become simultaneously effective if an observer looks into the multifocal intraocular lens simulator with his or her normal eye. Taking this into consideration, it is desirable for an index to be provided in a close vicinity of the real image formed in the afocal optical system to indicate a spacial position in the close vicinity of the real image, so that the observer gazes steadily at the index to thereby reduce the accommodation action of the eye to a minimum.

It is desirable for an angular magnification of the afocal optical system to be approximately 1. In other words, in order for the observer to perceive visibility similar to what he or she would actually perceive when wearing a multifocal intraocular lens, it is required that the observer can observe objects (external scenery, objects and others) through the optical system of the multifocal intraocular lens simulator at the same magnification as the naked eye. To achieve such an optical configuration, it is desirable for an angular magnification of the afocal optical system to be approximately 1.

Even if the angular magnification of the afocal optical system is not 1, the observer can perceive the optical effect of a test intraocular lens if only the pupil conjugate condition is satisfied; however, a sense of perspective in regard to objects viewed through the simulator differs from that in a state using the naked eye, so that the impression on the observer may differ.

It is possible for the afocal optical system to include two afocal optical systems which are substantially identical in magnifying power to each other and positioned to face each other. In a Keplerian afocal optical system, an erecting optical system (image-inverting optical system) such as a Porro prism is usually required to erect an inverted image. However, this erecting optical system (prism) simultaneously limits the angle of incident light on the optical system. In typical Keplarian binoculars, this incident angle is about ±10 degrees at the most even in binoculars with low magnifying power. In a Keplarian optical system with an angular magnification of approximately 1, the exit angle is also about the same, which narrows the apparent field of view. For this reason, the real field of view (apparent field of view) can be widened with the angular magnification being maintained at approximately 1 by replacing the erecting optical system by a relay optical system. More specifically, according to the optical arrangement of the afocal optical system that includes two afocal optical systems which are substantially identical in magnifying power to each other and positioned to face each other, objective lenses of the two afocal optical systems which are positioned to face each other function as a relay optical system and constitutes a Keplerian optical system, the angular magnification of which is approximately 1.

The aforementioned two afocal optical systems can be the same as those used for a pair of binoculars. Since a pair of binoculars contain a pair of afocal optical systems, respectively, the multifocal intraocular lens simulator according to the present invention incorporates a pair of test lens holders to correspond to the pair of afocal optical systems in the case where the multifocal intraocular lens simulator according to the present invention is designed as a binocular type.

It is desirable for an adjustable diaphragm to be installed in the afocal optical system so that, with a reduced aperture that is smaller in diameter than the pupil in a normal observing state of the observer, the observer can perceive visibility (how he or she sees objects) similar to what he or she would actually perceive due to the difference in visibility between different pupil diameters when wearing a multifocal intraocular lens. By stopping down the adjustable diaphragm, the aperture size of the adjustable diaphragm can be freely set if set to a size smaller in diameter than the pupil in a normal observing state of the observer.

It is possible for the test intraocular lens to include a multi focal intraocular lens which can be implanted in an eye as a substitution of a crystalline lens. Alternatively, a test piece optically equivalent to a multifocal intraocular lens can be used instead. As an example of an optically equivalent test piece, the test intraocular lens which is interchangeably held by the test lens holder can be one of a refractive-type test piece and a diffractive-type test piece. If the test intraocular lens is the refractive-type test piece, one of the following first and second conditions is satisfied: a first condition that a primary refractive power of the test intraocular lens that is held by the test lens holder is substantially zero, and a second condition that one of a first refractive power and a second refractive power of the test intraocular lens is zero while the other of the first refractive power and the second refractive power has a refractive portion having a differential refractive power. More specifically, the test piece can be made to have a non-refracting transmission portion with no refractive power and a refracting portion having a differential refractive power (e.g., 4D (diopter); corresponding to a difference between a primary refractive power (primary refractive power of a multifocal intraocular lens actually implanted in an eye; e.g., 20D (diopter)) and an additional refractive power). In the case of diffractive type, the test piece can be made so that O-order light as a primary refractive power has no refractive power and that 1-order light has the differential refractive power. It is desirable that the refractive-type test intraocular lens and the diffractive-type test piece be easily interchangeable when installed in the test lens holder so that the performances of the different type test pieces can be easily compared.

In other words, the optically equivalent test piece is made to have a portion having substantially no refractive power and a portion having a differential refractive power (e.g., 4D) which corresponds to a difference between the aforementioned primary refractive power and the aforementioned additional refractive power in the case of a refractive type, or made so that O-order light as a primary refractive power has no refractive power and that 1-order light has the differential refractive power in the case of a diffractive type.

In the case where an actual multifocal intraocular lens which can be actually implanted in an eye is used as a test intraocular lens, it is desirable for the test lens holder to include a liquid holding portion which holds a liquid, and for the multifocal intraocular lens and a compensator lens, which compensates for the primary refractive power of the multifocal intraocular lens, to be held in the liquid holding portion filled with the liquid.

It is desirable that a multifocal intraocular lens positioned in front of the afocal optical system be held in a liquid, such as water, contained in a liquid holding portion formed in the test lens holder because the primary function of the multifocal intraocular lens is determined as a substitution of that of a crystalline lens. On the other hand, since a multifocal intraocular lens has a refractive power of about 20D as a basic refractive power in water, if the lens is held simply held within parallel light rays in the vicinity of the entrance pupil of the afocal optical system, the observer wearing the multifocal intraocular lens experiences an extremely near-sighted state, and thus cannot observe distant scenery. Accordingly, it is desirable for the multifocal intraocular lens and a compensator lens having a negative refractive power, which cancels the primary refractive power of the multifocal intraocular lens, to be held in a liquid so that only a difference between the additional refractive power and the primary refractive power of the multifocal intraocular lens is extracted and relayed to the crystalline lens of the observer. In the case where a test piece optically equivalent to a multifocal intraocular lens is used, the compensator lens can be omitted by making the primary refractive power of the test piece zero.

In an embodiment, a method of simulating a multi focal intraocular lens is provided, including preparing an afocal optical system, wherein a parallel light bundle entering the afocal optical system is also substantially parallel when emerging therefrom; installing a prescribed test intraocular lens in front of the afocal optical system; and placing an eye of an observer at a position of an exit pupil of the afocal optical system to allow the observer to observe an object through the test intraocular lens and the afocal optical system.

In an embodiment, a method of simulating a multifocal intraocular lens is provided, including preparing an afocal optical system, wherein a parallel light bundle entering the afocal optical system is also substantially parallel when emerging therefrom; installing a front optical system and a prescribed test intraocular lens in front of the afocal optical system, the front optical system reducing an on-axis light bundle diameter of a light bundle incident on the front optical system before transmitting the light bundle toward the test intraocular lens; and placing an eye of an observer at a position of an exit pupil of the afocal optical system to allow the observer to observe an object through the front optical system, the test intraocular lens and the afocal optical system. A combined angular magnification of an entire optical system that includes the front optical system and the afocal optical system is approximately 1.

According to the present invention, one can actually perceive and experience the effect of multifocal intraocular lens implantation, the difference between diffractive type and refractive type, and also the demerits of a multifocal intraocular lens implantation without requiring multifocal intraocular lens implant surgery in order to perceive/experience such effects (i.e., before receiving multifocal intraocular lens implant surgery).

The present disclosure relates to subject matter contained in Japanese Patent Applications Nos. 2009-232502 (filed on Oct. 6, 2009), 2010-126673 (filed on Jun. 2, 2010), 2010-214672 (filed on Sep. 27, 2010) and 2010-214692 (filed on Sep. 27, 2010), which are expressly incorporated herein by reference in their entireties.

BRIEF DESCRIPTION OF THE DRAWINGS

The present invention will be described below in detail with reference to the accompanying drawings in which.

DESCRIPTION OF THE PREFERRED EMBODIMENTS

First Embodiment

Figure 1:
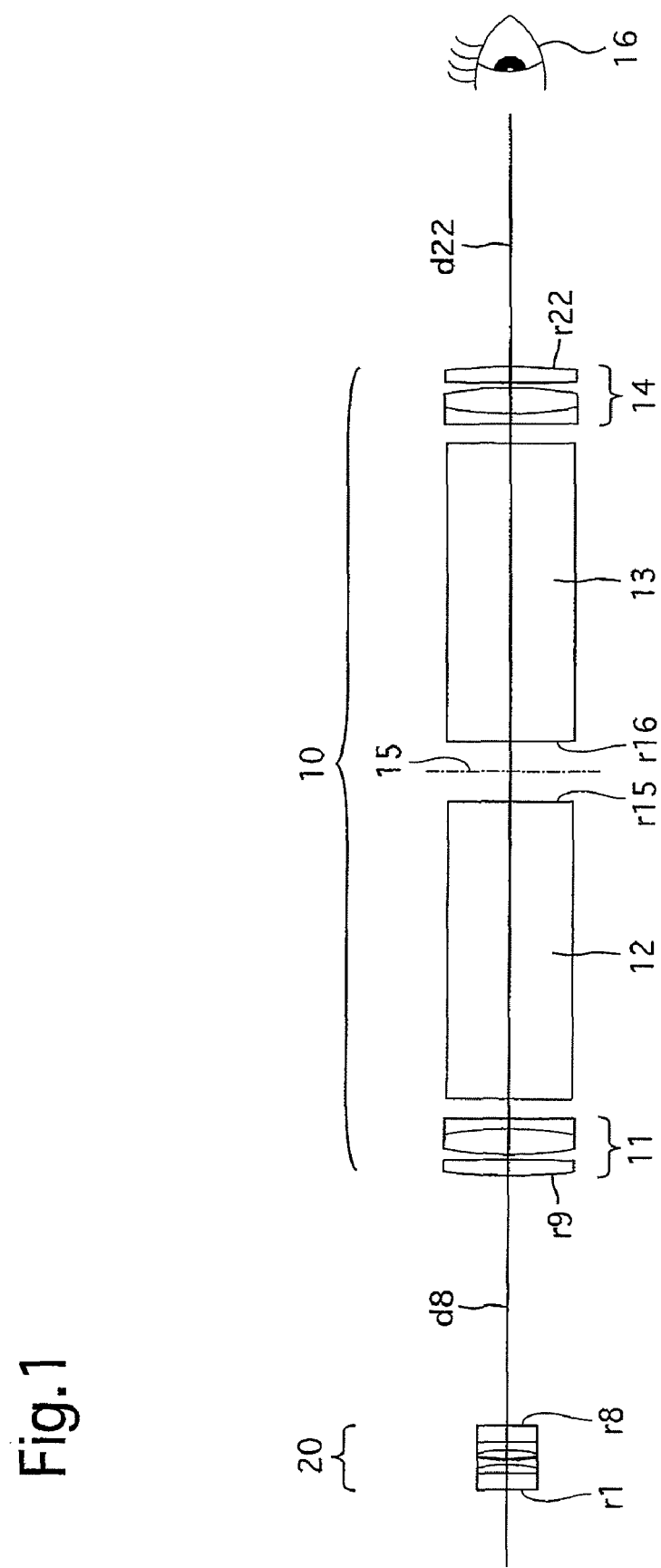
FIG. 1 is an optical diagram of an optical system provided in a first embodiment of a multifocal intraocular lens simulator according to the present invention.
Figure 2:
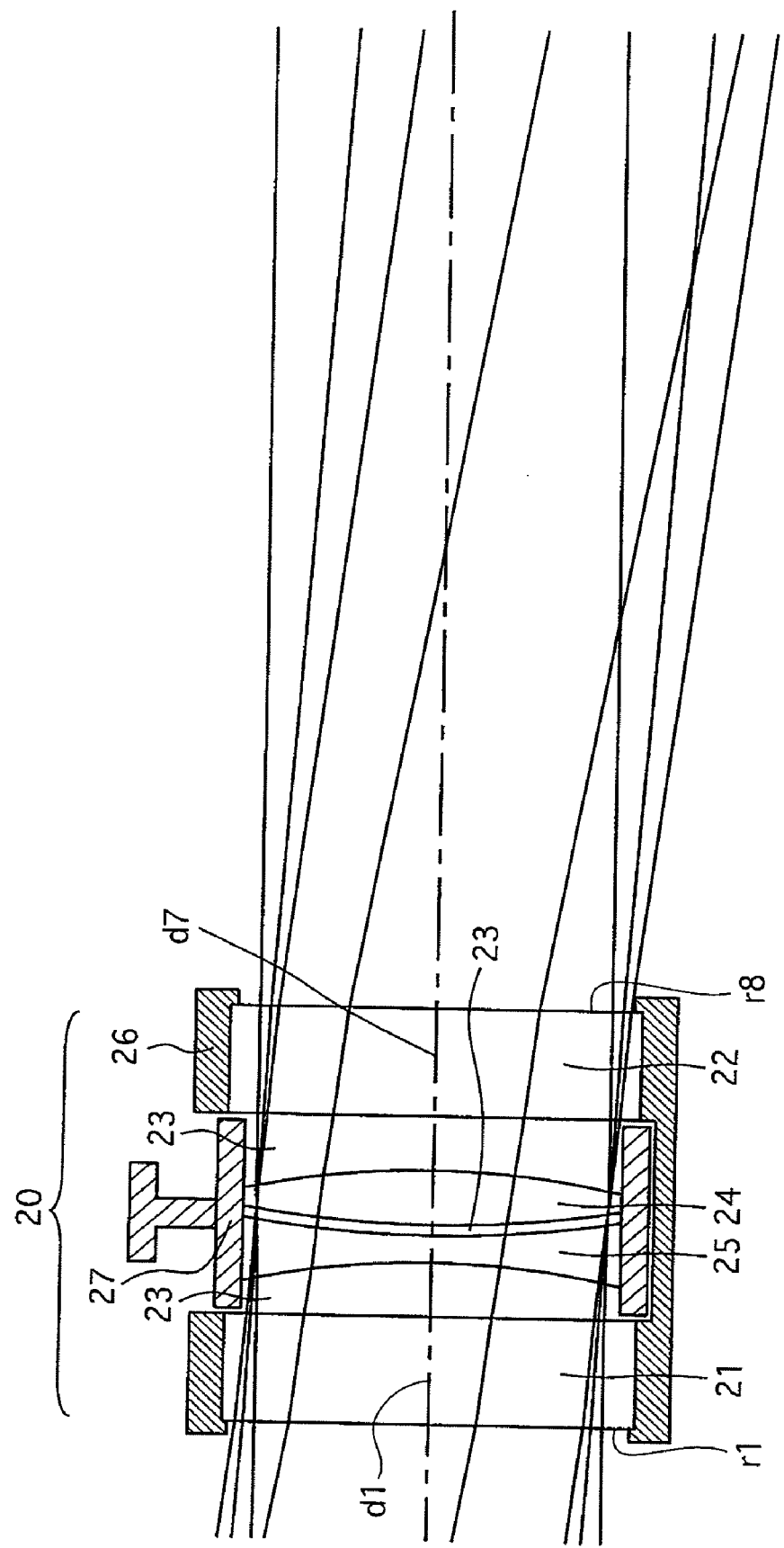
FIG. 2 is a cross sectional view of an embodiment of a test lens holder of the multifocal intraocular lens simulator that holds a multifocal intraocular lens (test lens) and a compensator lens contained in the optical system shown in FIG. 1.

FIGS. 1 and 2 show an optical system provided in a first embodiment of a multifocal IOL simulator according to the present invention. The optical system of the multifocal IOL simulator is provided with an afocal optical system 10, the angular magnification of which is approximately 1 (1.0×) and an IOL holder (test lens holder) 20 positioned at the entrance pupil of the afocal optical system 10. The afocal optical system 10 is designed such that parallel rays (rays from an infinite object) entering the afocal optical system 10 are also substantially parallel when emerging therefrom.

The afocal optical system 10 is provided with an objective lens group 11 having positive power, a first prism 12, a second prism 13 and an eyepiece lens group 14 having positive power, in that order from the object side. An image plane 15 is formed between the first prism 12 and the second prism 13. The objective lens group 11 and the first prism 12, and the second prism 13 and the eyepiece lens group 14 are symmetrically positioned with respect to the image plane 15. A real image of an object which is formed through the objective lens group 11 is formed on the image plane 15 (Keplerian type), and the image formed on the image plane 15 is seen through the eyepiece lens group 14 by an observer's eye 16 placed at the exit pupil of the afocal optical system 10. The first prism 12 and the second prism 13 serve as an erecting optical system and each have two reflecting surfaces, thus having four reflecting surfaces in total. More specifically, the first prism 12 and the second prism 13 can be configured from a double Porro prism. For instance, a reticle of crosshairs (index) formed (e.g., printed, engraved or embedded) on a transparent plate is installed at the image plane 15. The eyepiece lens group 14 is movable in an optical axis direction for diopter adjustment of the observer.

As shown in the enlarged view in FIG. 2, the TOL holder 20 is provided with a pair of transparent parallel plates (an incident plate and an exit plate) 21 and 22 which are spaced away from each other to define a liquid holding space 23 therebetween. The TOL holder 20 holds a multifocal TOL (test IOL) 24 and a compensator lens 25 in a liquid (water) contained in the liquid holding space 23. The IOL holder 20 is provided with a casing 26 and a removable lens holder 27 which can be removably installed in the casing 26. The transparent parallel plates 21 and 22 are fixed to the casing 26, and the removable lens holder 27 holds the multifocal IOL 24 and the compensator lens 25. When the multifocal IOL simulator is in an operating state, the liquid holding space 23 is filled with a liquid (water) with the multifocal IOL 24 and the compensator lens 25 inserted into the liquid holding space 23 in the casing 26. In addition, the IOL holder 20 is positioned so that the multifocal IOL 24 set in the liquid holding space 23 is positioned at the entrance pupil of the afocal optical system 10. Regardless of as to whether the multifocal IOL 24 is of refractive type or diffractive type, the multifocal IOL 24 has a primary refractive power (e.g., 20D) for use in water (as a substitution for body fluid) and an additional refractive power (e.g., 24D) which corresponds to the primary refractive power to which a differential refractive power (4D) is added. The compensator lens 25 has a negative refractive power which compensates for the primary refractive power of the multifocal TOL 24 to extract only a difference (4D) between the primary refractive power and the additional refractive power.

According to the afocal optical system 10 and the IOL holder 20, an observer can observe objects through the multifocal IOL 24 in the IOL holder 20 and the afocal optical system 10 from the rear thereof. Namely, the position of the exit pupil of the afocal optical system 10 is opened to allow an eye of the observer to be positioned thereat. In addition, the IOL holder 20 (the multifocal IOL 24) is installed at a position (pupil conjugate point) optically conjugate with the position where an eye (pupil) of the observer is to be placed, and accordingly, the optical effect of the multifocal IOL 24 of the IOL holder 20 positioned in front of the afocal optical system 10 can be relayed to the observer's eye 16 (the vicinity of the crystalline lens thereof) that is placed behind the afocal optical system 10, which makes it possible to have the observer perceive visibility similar to what he or she would actually perceive when wearing the multifocal IOL 24. The angular magnification of the afocal optical system 10 is 1, so that one can see objects (external scenery, objects, etc.) through the optical system of the multifocal intraocular lens simulator at the same magnification as the naked eye. It is desirable that the diameter of the entrance pupil of the afocal optical system 10 be greater than the diameter of the multifocal IOL 24.

By making the observer gaze steadily at the aforementioned reticle, which is installed (e.g., printed, engraved or embedded) at the image plane 15, the reticle functions to reduce the accommodation action of the eye to a minimum, thus making it easier for the observer to perceive the differential refractive power.

Numerical Embodiment 1 for the optical system shown in FIG. 1 will be discussed hereinafter.

Numerical Embodiment 1

TABLE 1 below shows lens data in Numerical Embodiment 1 for the optical system shown in FIG. 1. In each of TABLES 1, 2 and 4 through 8, NO designates the surface number counted from the object side, R designates the radius of curvature, d designates the lens-element thickness or the distance between lens elements (lens groups), N(d) designates the refractive index at the d-line, and v designates the Abbe number. The unit of R and the unit of d are mm (millimeters). The surface numbers 1 through 8 designate surfaces of the IOL holder 20 (the surface numbers 5 and 6 designate surfaces of the multifocal IOL 24), and the surface numbers 9 through 22 designate surfaces of the afocal optical system 10. The angle of incidence of light on the IOL holder 20 (angle of incidence of light on the afocal optical system 10) is ±10 degrees.

TABLE 1

| NO | R | d | N(d) | v | |
|----|---|---|------|---|---|
| 1 | ∞ | 2.000 | 1.51633 | 64.1 | |
| 2 | ∞ | 1.000 | 1.33304(water) | 55.8 | |
| 3 | −13.65 | 0.500 | 1.49176 | 57.4 | Compensator Lens |
| 4 | 17.9 | 0.200 | 1.33304(water) | 55.8 | |
| 5 | 17.9 | 1.000 | 1.49176 | 57.4 | IOL (20D) |
| 6 | −13.9 | 1.000 | 1.33304(water) | 55.8 | |
| 7 | ∞ | 2.000 | 1.51633 | 64.1 | |
| 8 | ∞ | 30.000 | | | |
| 9 | 61.392 | 1.920 | 1.69680 | 55.5 | |
| 10 | −205.56 | 0.600 | | | |
| 11 | 37.32 | 3.120 | 1.74400 | 44.9 | |
| 12 | −37.32 | 1.200 | 1.84666 | 23.8 | |
| 13 | 480 | 2.400 | | | |
| 14 | ∞ | 36.000 | 1.51633 | 64.1 | Prism |
| 15 | ∞ | 7.300 | | | |
| 16 | ∞ | 36.000 | 1.51633 | 64.1 | Prism |
| 17 | ∞ | 2.400 | | | |
| 18 | −480 | 1.200 | 1.84666 | 23.8 | |
| 19 | 37.32 | 3.120 | 1.74400 | 44.9 | |
| 20 | −37.32 | 0.600 | | | |
| 21 | 205.56 | 1.920 | 1.69680 | 55.5 | |
| 22 | −61.392 | 34.000 | | | |

Angular magnification of entire optical system=0.99

The image plane 15 (reticle) is positioned between the surface numbers 15 and 16 (see FIG. 1). The d-value 34 of the surface number 22 designates the distance (eye relief; designated by "d22" in FIG. 1) from the lens surface 22 to an eye point (at which marginal rays intersect the optical axis). In an ideal observing state, the position of the exit pupil of the afocal optical system 10 coincides with the aforementioned eye point.

Second Embodiment

Figure 3:
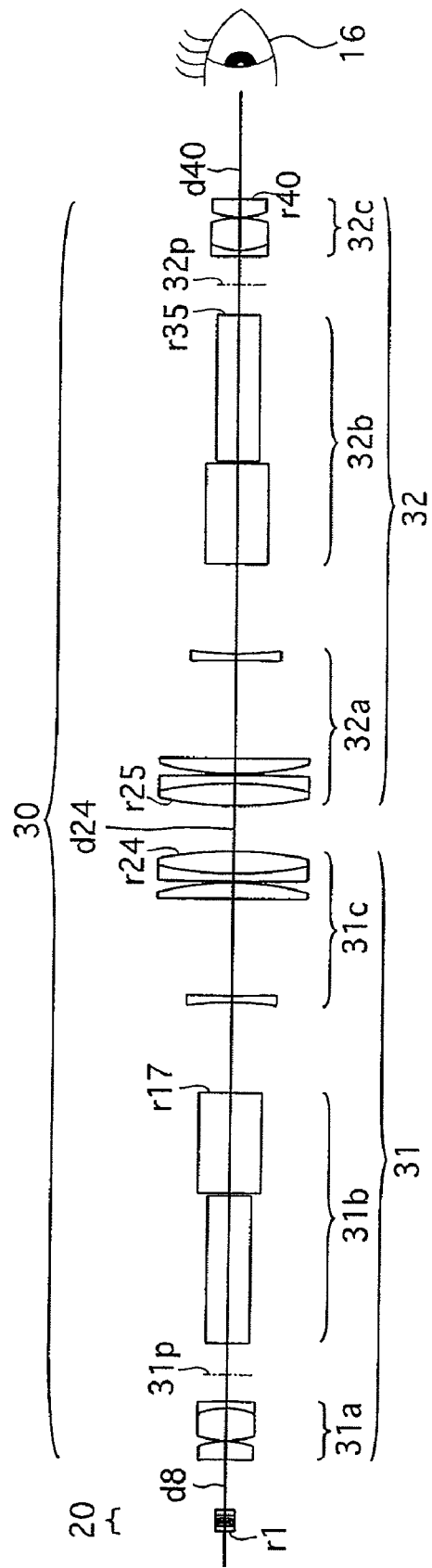
FIG. 3 is an optical diagram of an optical system provided in a second embodiment of the multifocal intraocular lens simulator according to the present invention.

FIG. 3 shows an optical system provided in a second embodiment of the multifocal IOL simulator according to the present invention. The optical system of this multifocal IOL simulator is provided with an afocal optical system 30, the angular magnification of which is approximately 1 and an IOL holder (test lens holder) 20 positioned at the entrance pupil of the afocal optical system 30. An observer's eye 16 is positioned at the exit pupil of the afocal optical system 30. The IOL holder 20 in the second embodiment of the multifocal IOL simulator is identical to that in the first embodiment of the multifocal TOL simulator.

The afocal optical system 30 is provided with two Keplerian afocal optical systems 31 and 32 which are symmetrically arranged. In this embodiment, the two Keplerian afocal optical systems 31 and 32 are configured from a pair of binocular optical systems (a pair of erecting binocular telescopes). The Keplerian afocal optical system 31, which is positioned toward the IOL holder 20, is provided with a positive lens group 31*a* (eyepiece lens group having positive power in the case of binoculars), an erecting optical system 31*b* having a total of four reflecting surfaces, and a positive lens group 31*c* (objective lens group having positive power in the case of binoculars), in that order from the object side. An image plane (primary image plane) 31*p* is formed between the positive lens group 31*a* and the erecting optical system 31*b*. The Keplerian afocal optical system 32, which is positioned toward the eye 16, is provided with a positive lens group 32*a* (objective lens group having positive power in the case of binoculars), an erecting optical system 32*b* having a total of four reflecting surfaces, and a positive lens group 32*c* (eyepiece lens group having positive power in the case of binoculars), in that order from the Keplerian afocal optical system 31 side. An image plane (secondary image plane) 32*p* is formed between the erecting optical system 32*b* and the positive lens group 32*c*. The positive lens group 31*a* and the positive lens group 32*c* are the same and symmetrically arranged, the erecting optical system 31*b* and the erecting optical system 32*b* are the same and symmetrically arranged, and the positive lens group 31*c* and the positive lens group 32*a* are the same and symmetrically arranged. A diopter adjustment capability and a focusing capability of a pair of binoculars can be adopted in a similar manner as for diopter adjustment for the observer of the multifocal IOL simulator.

Although the optical system of the multifocal IOL simulator contains the erecting optical system 31*b* and the erecting optical system 32*b* in the above described second embodiment shown in FIG. 3, since a pair of binocular optical systems are simply employed, the erecting optical system 31*b* and the erecting optical system 32*b* can be replaced by an optical system designed specifically for the multifocal IOL simulator. Each of the erecting optical system 31*b* and the erecting optical system 32*b* is configured from an erecting optical system (image-inverting optical system) such as a Porro prism; however, a Porro prism limits the angle of incidence of light on the afocal optical system 30. In contrast, by replacing this erecting optical system by a relay optical system, the angular magnification thereof is approximately 1 while at the same time the real field of view (apparent field of view) can be widened. In the case of the afocal, optical system 30 from which the erecting optical system 31*b* and the erecting optical system 32*b* are omitted, the positive lens group 31*c* of the Keplerian afocal optical system 31 and the positive lens group 32*a* of the Keplerian afocal optical system 32 that face each other function as a relay optical system and constitute a Keplerian optical system the angular magnification of which is approximately 1.

Additionally, since the afocal optical system 30, which employs a pair of binocular optical systems, includes a pair of afocal optical systems (configured from two Keplerian afocal optical systems 31 and 32 for the right eye and two Keplerian afocal optical systems 31 and 32 for the left eye, in which the right and left Keplerian afocal optical systems 31 constitute one pair of binoculars and the right and left Keplerian afocal optical systems 32 constitute another pair of binoculars), a multifocal intraocular lens simulator which allows an observer to use both eyes when viewing objects is achieved by providing the multifocal intraocular lens simulator with a pair of IOL holders, each corresponding to the IOL holder 20, to correspond to the pair of afocal optical systems 30. Even in the case where each of the afocal optical system 10 and the afocal optical system 30 is an optical system designed specifically for the multifocal intraocular lens simulator (i.e., even in the case where the multifocal intraocular lens simulator does not simply adopt a pair of afocal optical systems designed for binoculars), it is desirable that the multifocal intraocular lens simulator be provided with a pair of optical systems for both eyes, each of which includes the afocal optical system 10 or 30 and the IOL holder 20 shown in FIG. 1 or 3; however, a multifocal intraocular lens simulator can be provided with either of the optical systems shown in FIGS. 1 and 3 alone, rather than a pair, to be used as a multifocal intraocular lens simulator used for one eye at a time.

Figure 5:
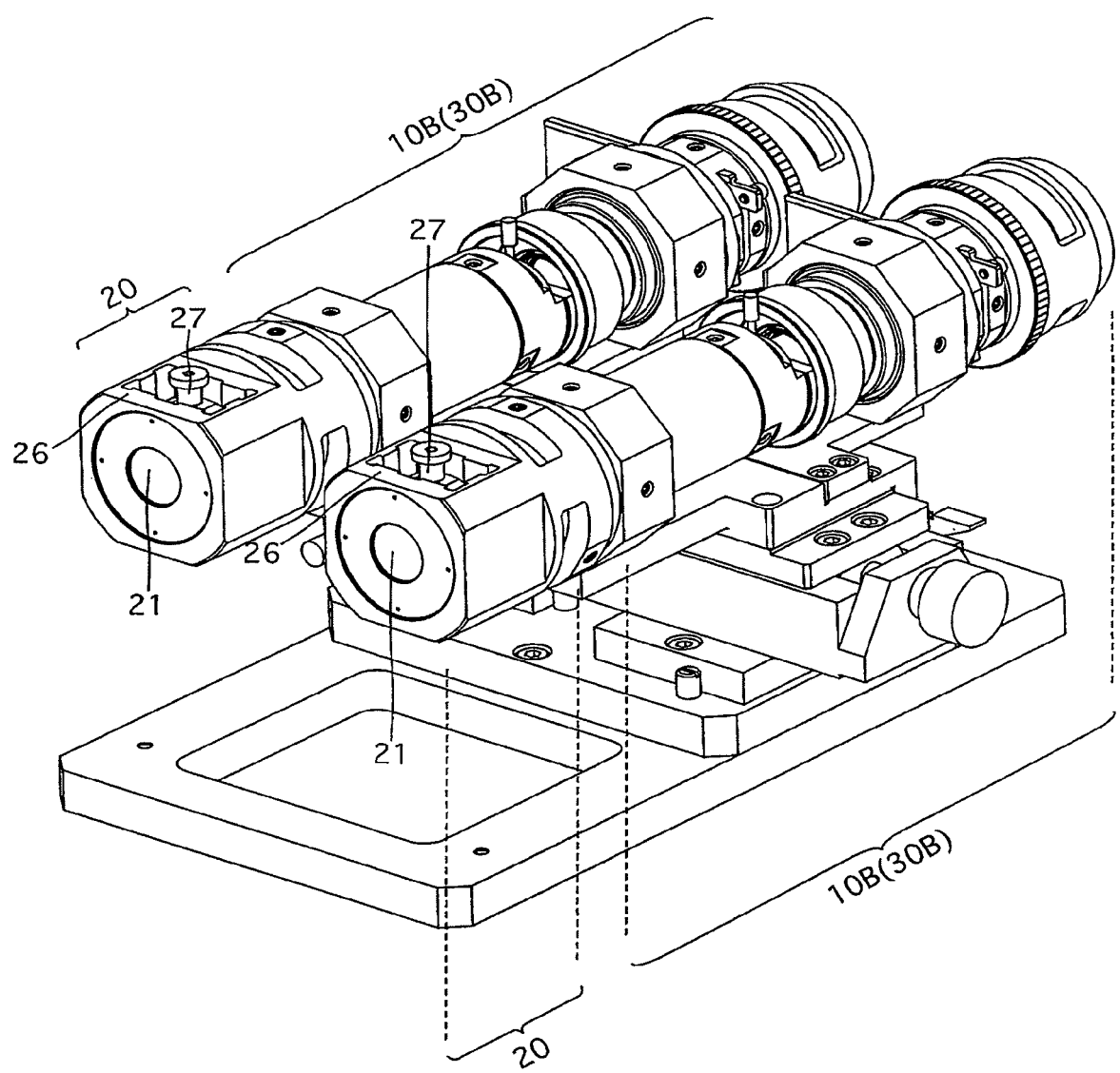
FIG. 5 is a perspective view of an embodiment of the multifocal intraocular lens simulator according to the present invention in the case where the multifocal intraocular lens simulator is constructed as a binocular type.

FIG. 5 shows an outward appearance of an embodiment of the multifocal intraocular lens simulator according to the present invention in the case where the multifocal intraocular lens simulator having the afocal optical system 10 shown in FIG. 1 or the afocal optical system 30 shown in FIG. 3 is constructed as a binocular type. This binocular-type multifocal intraocular lens simulator is provided with a pair of (right and left) optical barrels 10B, each of which contains the afocal optical system 10 shown in FIG. 1, or a pair of optical barrels 30B, each of which contains the afocal optical system 30 shown in FIG. 3. The front ends of the pair of optical barrels 10B or 30B are each provided at the front end thereof with the IOL holder 20 shown in FIG. 2. According to this binocular-type multifocal intraocular lens simulator, one can actually perceive the simulation effect through both eyes (binocular vision).

Numerical Embodiment 2 for the optical system shown in FIG. 3 will be discussed hereinafter.

Numerical Embodiment 2

TABLE 2 below shows lens data in Numerical Embodiment 2 for the optical system shown in FIG. 3. The surface numbers 1 through 8 designate surfaces of the IOL holder 20 (the surface numbers 5 and 6 designate surfaces of the multifocal IOL 24), and the surface numbers 9 through 24 designate surfaces of the Keplerian afocal optical system 31, and the surface numbers 25 through 40 designate surfaces of the Keplerian afocal optical system 32. The Keplerian afocal optical system 31 and the Keplerian afocal optical system 32 are mutually identical, each having an angular magnification of 8 (8×). The angle of incidence of light on the IOL holder 20 (angle of incidence of light on the afocal optical system 31) is ±20 degrees. In the embodiment shown in FIG. 3, an adjustable diaphragm can be installed. A position in between the two Keplerian afocal optical systems 31 and 32 is optically conjugate with the position of the IOL holder 20, so that installing an adjustable diaphragm at this optically conjugate position makes it possible to uniformly narrow down a light bundle incident from all angles on the afocal optical system 30 (32).

TABLE 2

| NO | R | d | N(d) | ν | |
|----|---|---|------|---|---|
| 1 | ∞ | 2.000 | 1.51633 | 64.1 | |
| 2 | ∞ | 1.000 | 1.33304(water) | 55.8 | |
| 3 | −13.65 | 0.500 | 1.49176 | 57.4 | Compensator Lens |
| 4 | 17.9 | 0.200 | 1.33304(water) | 55.8 | |
| 5 | 17.9 | 1.000 | 1.49176 | 57.4 | IOL (20D) |
| 6 | −13.9 | 1.000 | 1.33304(water) | 55.8 | |
| 7 | ∞ | 2.000 | 1.51633 | 64.1 | |
| 8 | ∞ | 18.000 | | | |
| 9 | −336.4 | 6.496 | 1.62041 | 60.3 | |
| 10 | −22.388 | 0.232 | | | |
| 11 | 26.448 | 11.600 | 1.62041 | 60.3 | |
| 12 | −21.46 | 2.320 | 1.80518 | 25.5 | |
| 13 | −188.5 | 20.834 | | | |
| 14 | ∞ | 52.850 | 1.51680 | 64.2 | |
| 15 | ∞ | 0.928 | | | |
| 16 | ∞ | 36.285 | 1.56883 | 56.0 | |
| 17 | ∞ | 32.434 | | | |
| 18 | −93.448 | 2.320 | 1.51742 | 52.2 | |
| 19 | 485.008 | 35.102 | | | |
| 20 | ∞ | 5.800 | 1.51680 | 64.2 | |
| 21 | −87.904 | 0.348 | | | |
| 22 | 734.524 | 2.900 | 1.69895 | 30.0 | |
| 23 | 111.558 | 8.120 | 1.51680 | 64.2 | |
| 24 | −111.558 | 16.240 | | | |
| 25 | 111.558 | 8.120 | 1.51680 | 64.2 | |
| 26 | −111.558 | 2.900 | 1.69895 | 30.0 | |
| 27 | −734.524 | 0.348 | | | |
| 28 | 87.904 | 5.800 | 1.51680 | 64.2 | |
| 29 | ∞ | 35.102 | | | |
| 30 | −485.008 | 2.320 | 1.51742 | 52.2 | |
| 31 | 93.448 | 32.434 | | | |
| 32 | ∞ | 36.285 | 1.56883 | 56.0 | |
| 33 | ∞ | 0.928 | | | |
| 34 | ∞ | 52.850 | 1.51680 | 64.2 | |
| 35 | ∞ | 20.834 | | | |
| 36 | 188.5 | 2.320 | 1.80518 | 25.5 | |
| 37 | 21.46 | 11.600 | 1.62041 | 60.3 | |
| 38 | −26.448 | 0.232 | | | |
| 39 | 22.388 | 6.496 | 1.62041 | 60.3 | |
| 40 | 336.4 | 20.000 | | | |

Angular magnification of entire optical system=0.99

An index (e.g., a reticle) is positioned at a distance 8.12 mm behind the exit surface (NO. 35) of the erecting optical system 32b (at the image plane 32p). The d value 20.00 of the surface number 40 designates the distance in millimeters (eye relief; designated by "d40" in FIG. 3) from the lens surface 40 to an eye point (at which marginal rays intersect the optical axis). In an ideal observing state, the position of the exit pupil of the afocal optical system 30 coincides with this eye point.

Figure 4:
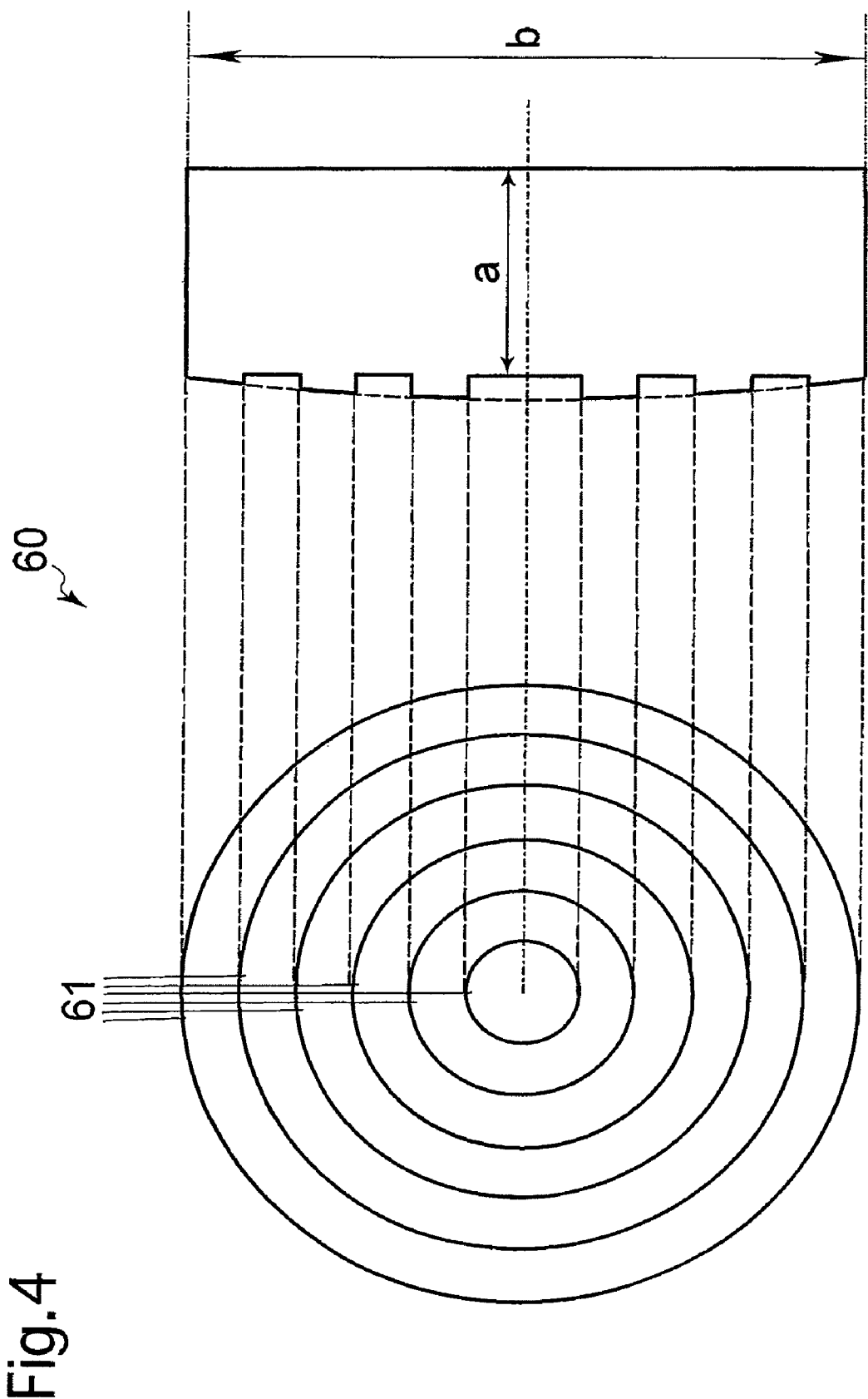
FIG. 4 is a schematic illustration of a refractive-type test piece, showing the structure thereof.

In the above described embodiments, the multifocal IOL 24 is used as a test IOL; however, a test piece optically equivalent to the multifocal IOL 24 can be used instead. FIG. 4 is a schematic illustration of a refractive-type test piece 60 that is designed as a substitution of a refractive-type bifocal intraocular lens, showing the structure thereof. The test piece 60 is formed to have a primary refractive power of OD (0 diopter) for distance vision, thus allowing a negative compensation lens to be omitted. The front surface of the test piece 60 is provided with a six concentric ring structure 61. A light bundle passing through concentric parallel-surface portions (recessed portions) of the front surface of the test piece 60 shown in FIG. 4 take charge of distant focusing, while a light bundle passing through concentric convex surface portions of the front surface of the test piece 60 shown in FIG. 4 take charge of near focusing. TABLE 3 below shows parameters of the test piece 60. In TABLE 3, r designates the radius of curvature of each convex surface portion (mm), n1 designates the refractive index, f designates the focal length of each convex surface portion (mm), D designates the diopter for near vision (differential refractive power), and Sag designates the amount of sagitta of the (stepped) central ring band portion (mm). Additionally, a center thickness a (shown by a double-headed arrow in FIG. 4) is, e.g., 2 mm and an outer diameter b (shown by a double-headed arrow in FIG. 4) is, e.g., 6 mm.

TABLE 3

| | |
|---|---|
| r | 41 |
| n1 | 1.5 |
| f | 250 |
| D | 4.00 |
| Sag | 0.11 |

FIGS. 6 through 12 show more embodiments of the multifocal intraocular lens simulators according to the present invention. These embodiments have the capability of compensating for corneal effects.

Third Embodiment

Figure 6:
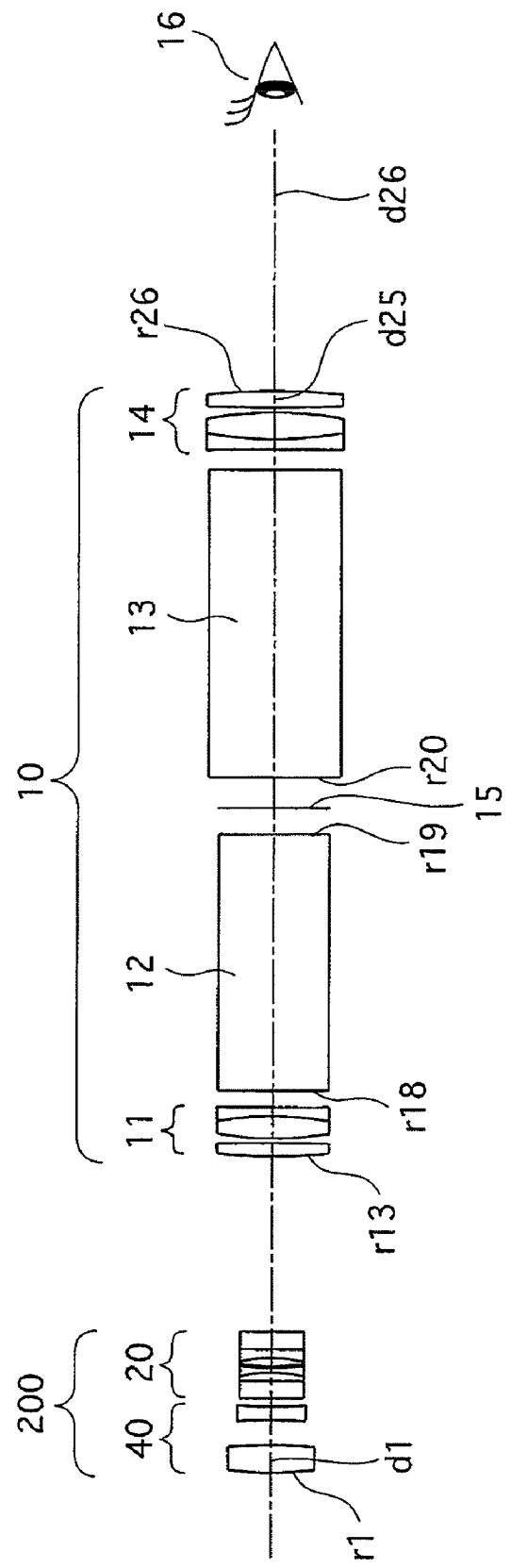
FIG. 6 is an optical diagram of an optical system provided in a first embodiment of a corneal effect compensation type of multifocal intraocular lens simulator according to the present invention.
Figure 7:
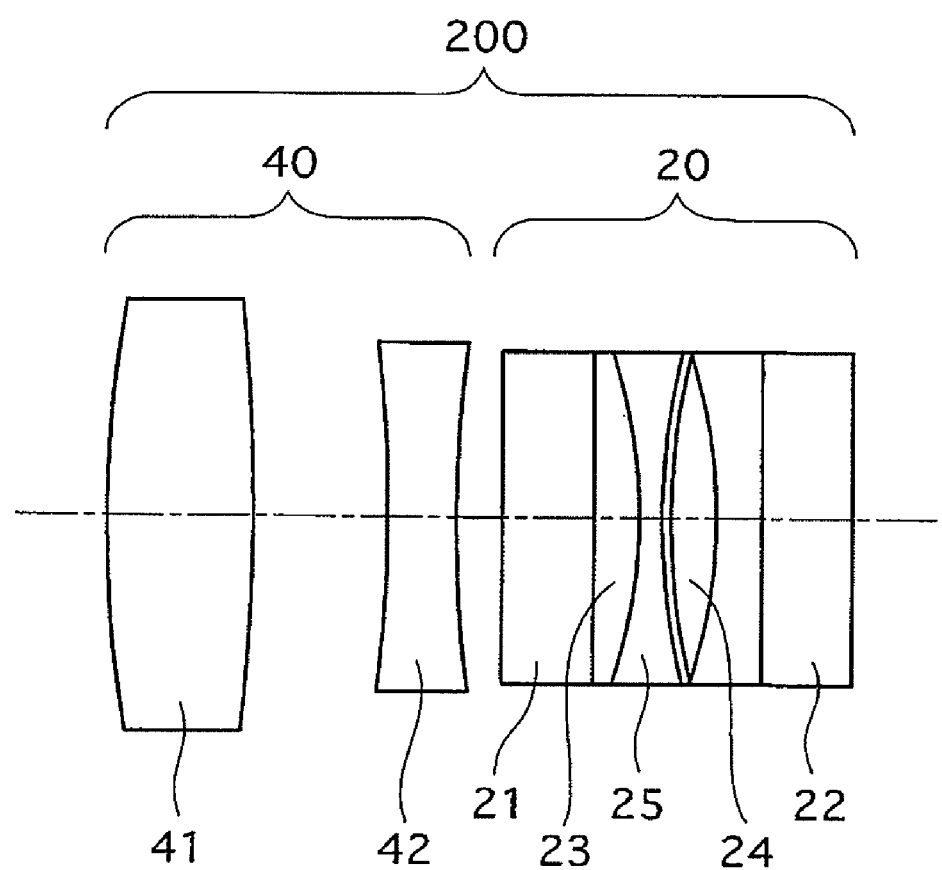
FIG. 7 is an enlarged cross sectional view of an embodiment of a portion of the optical system shown in FIG. 6 in the vicinity of a multifocal intraocular lens (test lens) thereof.
Figure 8:
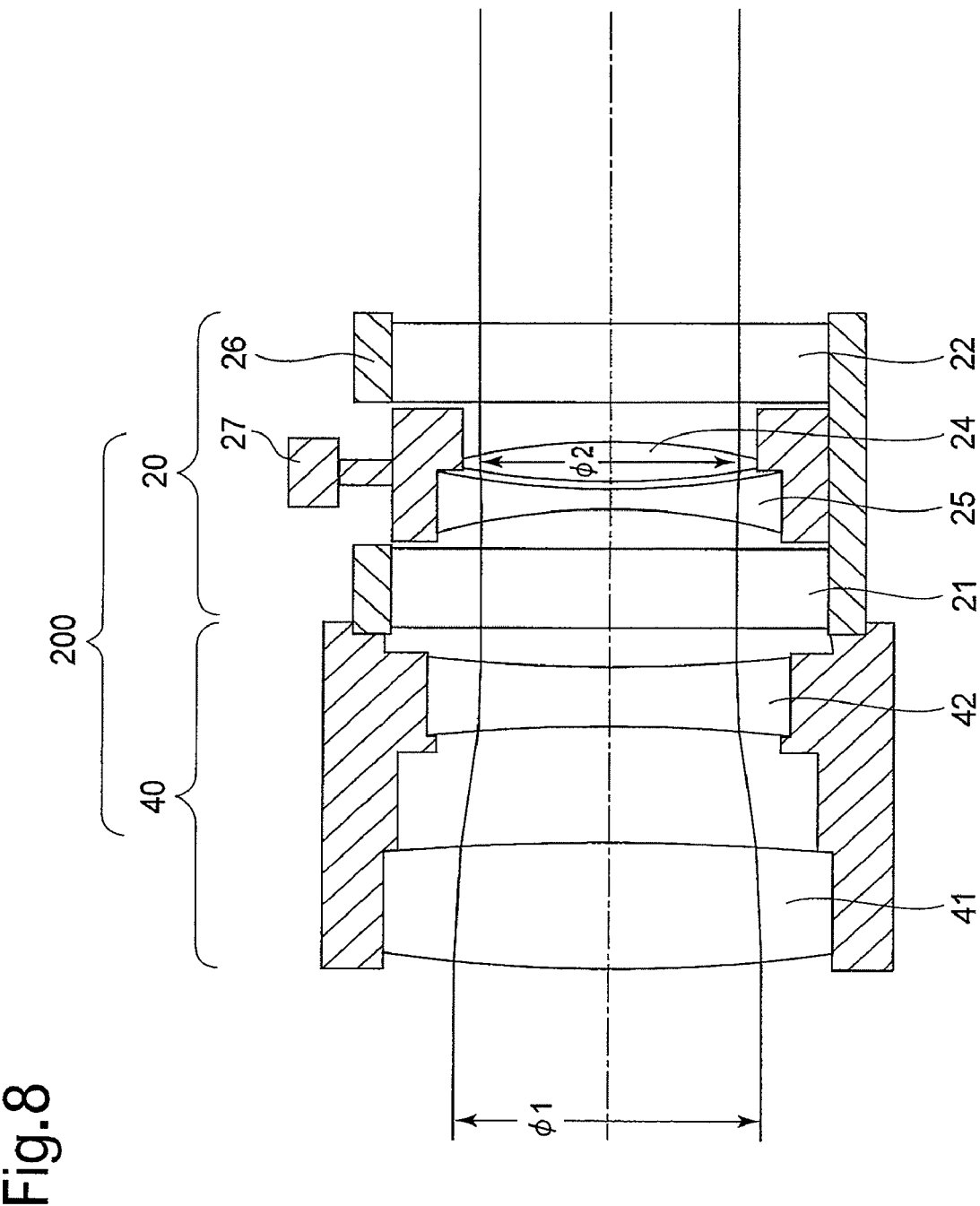
FIG. 8 is a cross sectional view of an embodiment of a test lens holder that holds an intraocular lens optical system shown in FIG. 7.

FIGS. 6 through 8 show an optical system provided in a third embodiment of the multifocal IOL simulator according to the present invention, specifically a first embodiment of a corneal effect compensation type of multifocal intraocular lens simulator according to the present invention. The optical system of this multifocal IOL simulator is provided with an afocal optical system (primary afocal optical system) 10 and an IOL optical system 200 positioned at the entrance pupil of the afocal optical system 10. The afocal optical system 10 of this optical system is identical to that shown in FIG. 1. An infinite-object emanated light bundle (parallel light bundle) entering the afocal optical system 10 is also substantially parallel when it exits.

Similar to the afocal optical system 10 shown in FIG. 1, the afocal optical system 10 shown in FIG. 6 is a so-called Keplerian afocal optical system and provided with an objective lens group 11 having a positive power, a first prism 12, a second prism 13 and an eyepiece lens group 14 having positive power in that order from the object side. A real image of an object which is formed through the objective lens group 11 is formed on the image plane 15, and the image formed on the image plane 15 is seen through the eyepiece lens group 14 by an observer's eye 16 placed at the exit pupil of the afocal optical system 10. Further descriptions of the afocal optical system 10 shown in FIG. 6 are omitted since the afocal optical system 10 shown in FIG. 6 is the same as that described with reference to FIG. 1.

The IOL optical system 200 is provided with an IOL holder 20 and a front optical system (magnifying optical system) 40 positioned in front of the IOL holder 20. The IOL holder 20 of the IOL optical system 200 is the same as that described with reference to FIG. 2, thus holding a multifocal IOL 24 and a compensator lens 25 therein as shown in FIG. 2. As described above, the multifocal IOL (test IOL) 24 and the compensator lens 25 are removably supported by a removable lens holder 27 (see FIG. 8) which can be removably installed in the casing 26. The liquid holding space 23 of the IOL optical system 200 is positioned at the entrance pupil of the afocal optical system 10. Regardless of as to whether the multifocal IOL 24 is of refractive type or diffractive type, the multifocal IOL 24 has a primary refractive power (e.g., 20D) for use in water (as a substitution of body fluid) and an additional refractive power (e.g., 24D) which corresponds to the primary refractive power to which a differential refractive power is added. The compensator lens 25 has a negative refractive power which compensates for the primary refractive power of the multifocal IOL 24 to extract only a difference (4D) between the primary refractive power and the additional refractive power. The angle of incidence of light on the TOL optical system 200 shown in FIG. 7 is ±10 degrees. FIG. 8 shows an embodiment of a test lens holder for the IOL optical system 200 that includes the IOL holder 20 and the front optical system 40.

The compensator lens 25 can be omitted if a test piece with no primary refractive power to which only a differential refractive power is given is used instead of a multifocal IOL. In addition, since the rays of light incident on and emerging from the liquid holding space 23 are afocal rays in the first embodiment of the corneal effect compensation type of multifocal intraocular lens simulator shown in FIGS. 6 through 8, this test piece can be designed to relay a prescribed differential refractive power to the observer when being held in a liquid (water) or air. If the test piece is for use in air, the liquid (water) contained in the liquid holding space 23 only needs to be drained therefrom to empty the liquid holding space 23 before the test piece is installed therein.

The front optical system 40 is configured from a Galilean afocal system consisting of a positive lens element 41 and a negative lens element 42 and simulates effects of the positive refractive power of a cornea. Accordingly, in the case where a crystalline lens is actually removed to be replaced by an IOL, light bundle incident on the IOL is converged due to the effect of a cornea, so that the diameter of the light bundle on the cornea and the diameter of the light bundle on the IOL are mutually different. In contrast, by installing the front optical system 40 that produces an effect (which will be discussed later) in the IOL optical system 200, the multifocal IOL lens 24 can be evaluated with the diameters of an incident light bundle and an exit light bundle on the front surface and from the rear surface of the multifocal IOL lens 24 (test lens) having been made equal to the diameters of those on the front surface and from the rear surface of the multifocal IOL lens 24, respectively, actually implanted in an eye.

The angular magnification of the front optical system 40 is determined so that the entire optical system of the multifocal IOL simulator shown in FIG. 6 becomes approximately 1 in consideration of the combined angular magnification of the front optical system 40 and the afocal optical system 10. More specifically, in the case where the angular magnification of the front optical system 40 is set to approximately 1.2, the angular magnification of the entire optical system can be made approximately 1 by setting the angular magnification of the afocal optical system 10 to approximately 0.83(=1/1.2). In this embodiment, the IOL holder 20 that includes the multifocal IOL 24 and the compensator lens 25 only has the residual differential refractive power. By setting the powers of the front optical system 40, the afocal optical system 10 and the compensator lens 25 in such a manner, the ratio of the diameter of the exit pupil of the afocal optical system 10 in the vicinity of the crystalline lens of the eye 16 to the diameter of the entrance pupil of the afocal optical system 10 in the vicinity of the multifocal IOL 24, i.e., the pupil magnification of the entire optical system shown in FIG. 6 is set to approximately 1, so that the effect of the differential refractive power among optical effects of the multifocal IOL 24 can be relayed to a vicinity of the observer's crystalline lens with high precision.

More specifically, in order to relay the optical effect of the multifocal IOL 24 to a vicinity of a crystalline lens of the observer of the present embodiment of the corneal effect compensation type of multifocal intraocular lens simulator with higher precision, it is desirable that the pupil diameter (on-axis light bundle diameter) in the present embodiment of the multifocal intraocular lens simulator at the position of a test IOL installed therein and the pupil diameter (on-axis light bundle diameter) in the same multifocal intraocular lens simulator at the position of an observer's crystalline lens be substantially identical to each other. This means to make the pupil diameter (on-axis light bundle diameter) of a test IOL installed in the present embodiment of the multifocal intraocular lens simulator and the pupil diameter (on-axis light bundle diameter) of a light bundle passing through the same IOL implanted in an eye substantially equal to each other. Since the refractive power (optical effect) of the multifocal IOL 24 is relayed to an observer's eye in proportion to the second power of the pupil diameter in the present embodiment of the multifocal intraocular lens simulator, the accuracy of simulation considerably deteriorates if the difference between the pupil diameter of the multifocal IOL 24 before implantation and the pupil diameter of the multifocal IOL 24 after implantation is great. Based on numerical values of the traditional Le-Grand eye model, it is known in the art that the pupil diameter of a crystalline lens is reduced approximately 0.89 times and approximately 0.77 times at the incident surface and the exit surface of the crystalline lens, respectively, with respect to the diameter of a light bundle (on-axis light bundle diameter) incident on an observer's cornea. Therefore, the optical effect of the multifocal IOL 24 can be relayed to the observer's eye 16 in contemplation of the relationship between the on-axis light bundle diameter at the multifocal IOL 24 and the on-axis light bundle diameter at the afocal optical system 10 on the exit surface side thereof (i.e., the diameter of an incident light beam on an observer's cornea) in addition to the relationship with the aforementioned reductions in pupil diameter. Namely, it is desirable that the pupil magnification of the afocal optical system 10 (=the diameter of the exit pupil/the diameter of the entrance pupil) be determined in consideration of the relationship with the aforementioned reductions in pupil diameter. In the case where the reduction magnification of the pupil diameter at the position of a crystalline lens is assumed to be approximately 0.83 on average since it is 0.89-0.77 in Le-Grand eye model, the relationship between the on-axis light bundle diameter at the multifocal intraocular lens 24 and the diameter of an incident light bundle on an observer's cornea can be set to be close to that of a state where the multifocal IOL 24 is actually implanted in an eye by setting the pupil magnification of the afocal optical system 10 to 1/0.83 (=1.2 times; at this time the angular magnification is 0.83 times). However, if the optical system shown in FIG. 6 includes only the afocal optical system 10, the angular magnification of the optical system shown in FIG. 6 is 0.83, and therefore, perspective of objects (external scenery, objects and others) will not be adequately reflected. Accordingly, the addition of the front optical system 40 (Galilean afocal system) with an angular magnification of approximately 1.2 in front of the IOL holder 20 allows a light bundle which is magnified 0.83 times to pass through the multifocal IOL 24 and allows the angular magnification of the entire optical system of the present embodiment of the multifocal intraocular lens simulator to be 1.0 (0.83 times of the afocal optical system 10×1.2 times of the front optical system 40=1.0 time) while maintaining an appropriate visual perception of perspective of objects which are seen through the simulator.

According to the above described corneal effect compensation type of multifocal intraocular lens simulator, in a state where even the effect of the positive refractive power of a cornea is simulated, the observer can see objects via a light bundle which is passed through the front optical system 40, the multifocal IOL 24 and the afocal optical system 10, in that order. More specifically, since the IOL holder 20 (the multifocal IOL 24) is arranged at a position (pupil conjugate point) optically conjugate with the position of the exit pupil of the afocal optical system 10, where an eye of the observer is to be placed, and also since the IOL optical system 200 is provided at the front thereof with the front optical system 40 for simulating the effect of a cornea, the optical effect of the multifocal IOL 24 contained in the IOL optical system 200 that is positioned in front of the afocal optical system 10 can be relayed, in consideration of corneal effects, to the observer's eye 16 (at or at a close vicinity of the crystalline lens thereof) that is positioned behind the afocal optical system 10, which makes it possible to have the observer perceive visibility similar to what he or she would actually perceive when wearing the multifocal IOL 24. The combined angular magnification of the entire optical system shown in FIG. 6, ranging from the front optical system 40 to the afocal optical system 10, is 1, so that one can see objects (external scenery, objects, etc.) through the optical system of the multifocal intraocular lens simulator at the same magnification as the naked eye. It is desirable that the diameter of the entrance pupil (diameter of a full-open mechanical aperture) of the afocal optical system 10 be greater than the diameter of the multifocal IOL 24.

Numerical Embodiment 3 for the optical system shown in FIG. 6 will be discussed hereinafter.

Numerical Embodiment 3

TABLE 4 below shows lens data in Numerical Embodiment 3 for the optical system shown in FIG. 6. The surface numbers 1 through 6 designate surfaces of the front optical system 40 (it should be noted that the transparent parallel plate 21 also serves as an element of the front optical system 40), the surface numbers 7 and 8 designate surfaces of the compensator lens 25, the surface numbers 9 and 10 designate surfaces of the multifocal IOL 24, and the surface numbers 13 through 26 designate surfaces of the afocal optical system 10. Lens data on the surface numbers 5 through 26 shown in TABLE 3 are identical to lens data on the surface numbers 1 through 22 shown in TABLE 1.

TABLE 4

| NO | R | d | N (d) | ν (d) |
|----|---|---|-------|-------|
| 1 | 33.000 | 3.200 | 1.77250 | 49.6 |
| 2 | −54.300 | 2.930 | | |
| 3 | −36.400 | 1.500 | 1.80100 | 35.0 |
| 4 | 36.400 | 1.000 | | |
| 5 | ∞ | 2.000 | 1.51633 | 64.1 |
| 6 | ∞ | 1.000 | 1.33304 (water) | 55.8 |
| 7 | −13.650 | 0.500 | 1.49176 | 57.4 (compensator lens) |
| 8 | 17.900 | 0.200 | 1.33304 (water) | 55.8 |
| 9 | 17.900 | 1.000 | 1.49176 | 57.4 (IOL (20D)) |
| 10 | −13.900 | 1.000 | 1.33304 (water) | 55.8 |
| 11 | ∞ | 2.000 | 1.51633 | 64.1 |
| 12 | ∞ | 20.500 | | |
| 13 | 51.160 | 1.600 | 1.69680 | 55.5 |
| 14 | −171.300 | 0.500 | | |
| 15 | 31.100 | 2.600 | 1.74400 | 44.9 |
| 16 | −31.100 | 1.000 | 1.84666 | 23.8 |
| 17 | 400.000 | 2.000 | | |
| 18 | ∞ | 30.000 | 1.51633 | 64.1 (prism 12) |
| 19 | ∞ | 6.690 | | |
| 20 | ∞ | 36.000 | 1.51633 | 64.1 (prism 13) |
| 21 | ∞ | 2.400 | | |
| 22 | −480.000 | 1.200 | 1.84666 | 23.8 |
| 23 | 37.320 | 3.120 | 1.74400 | 44.9 |
| 24 | −37.320 | 0.600 | | |
| 25 | 205.560 | 1.920 | 1.69680 | 55.5 |
| 26 | −61.392 | 34.0 | | |

Angular magnification of entire optical system = 0.98
Diameter of on-axis light bundle incident on front optical system φ1 = 7.08
Diameter of on-axis light bundle emerging from front optical system to proceed toward test IOL φ2 = 5.98 φ2/φ1 = 0.84

An index (e.g., a reticle) is positioned at the image plane 15 between the surface numbers 19 and 20. The d value 34 of the surface number 26 designates the distance (eye relief; designated by "d26" in FIG. 6) from the lens surface 26 to an eye point (at which marginal rays intersect the optical axis). In an ideal observing state, the position of the exit pupil of the afocal optical system 10 coincides with the aforementioned eye point.

Fourth Embodiment

Figure 9:
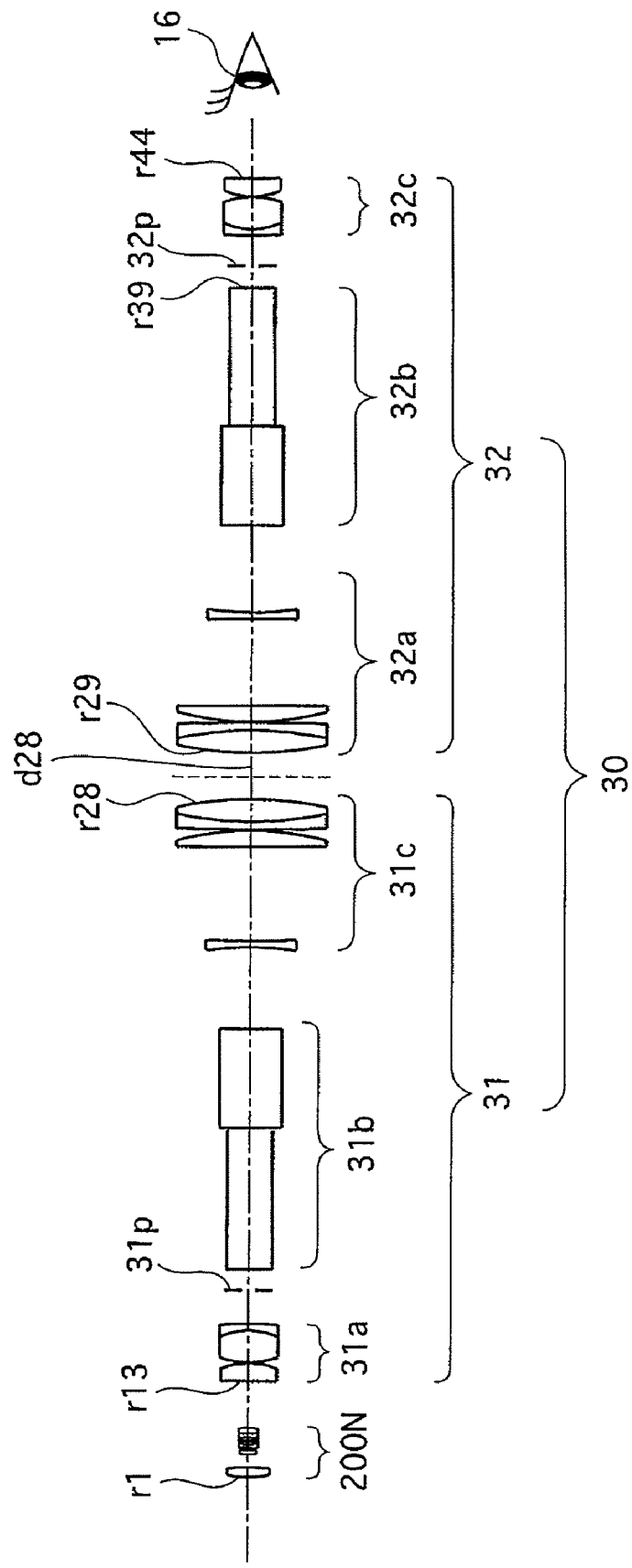
FIG. 9 is an optical diagram of an optical system provided in a second embodiment of the corneal effect compensation type of multifocal intraocular lens simulator according to the present invention.
Figure 10:
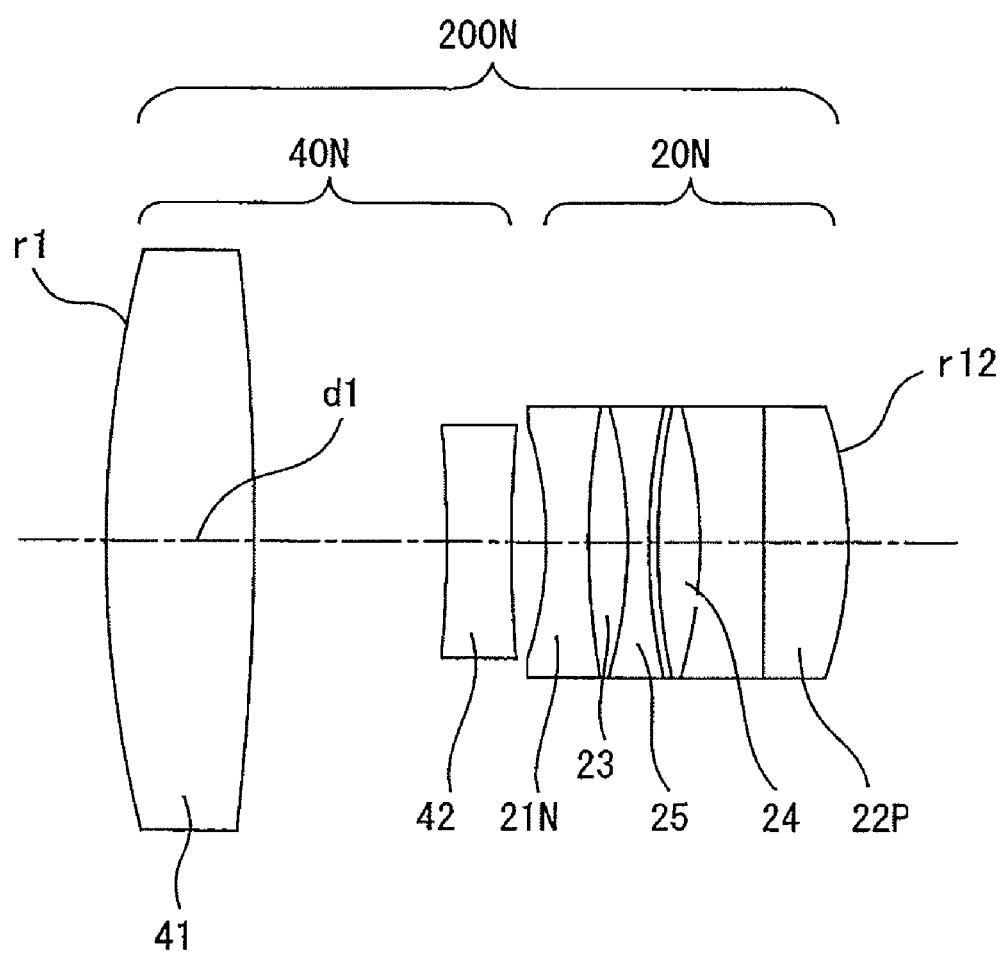
FIG. 10 is an enlarged cross sectional view of a portion of the optical system shown in FIG. 9 in the vicinity of a multifocal intraocular lens (test lens) thereof.
Figure 11:
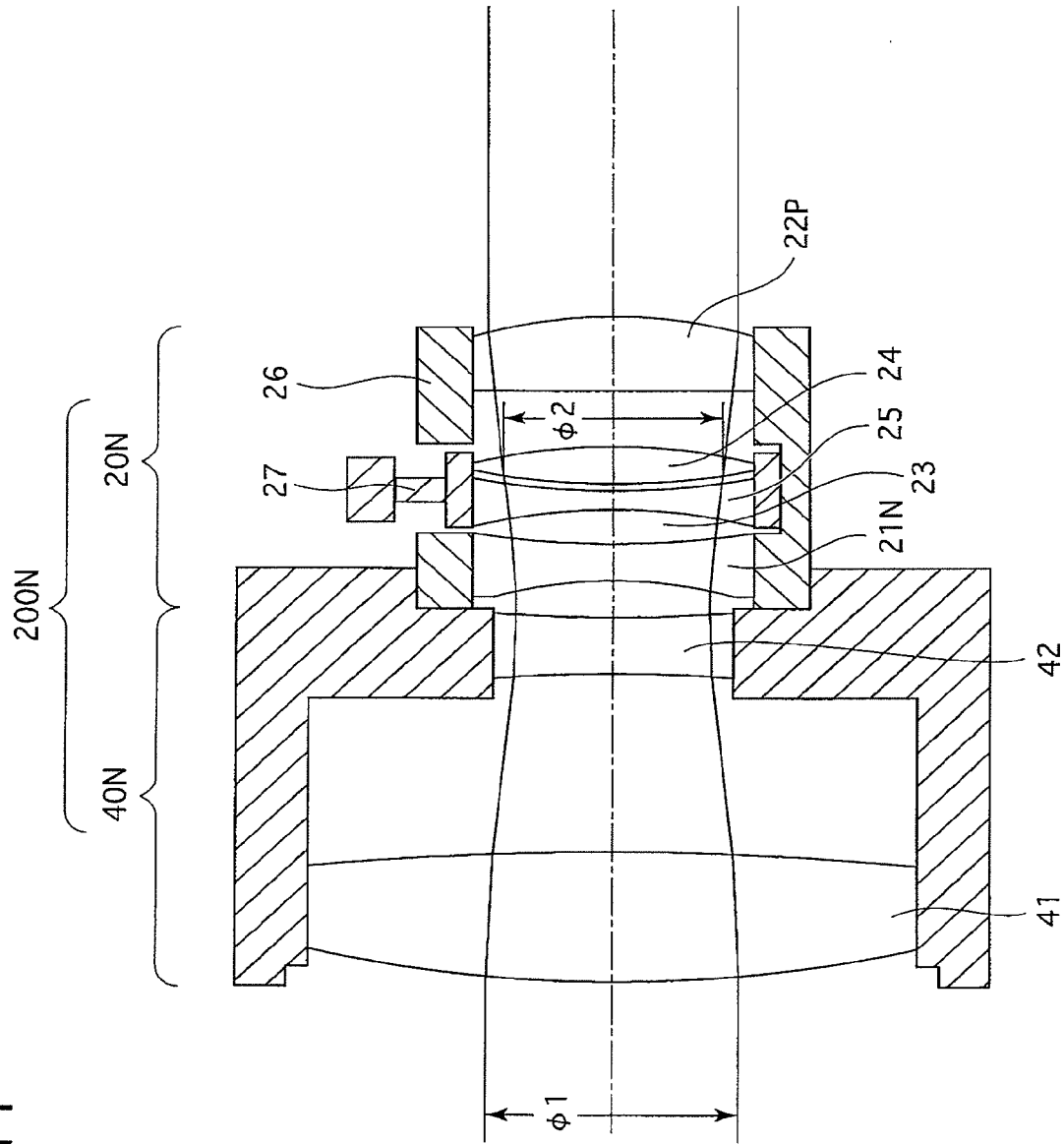
FIG. 11 is a cross sectional view of an embodiment of a test lens holder for an intraocular lens optical system shown in FIGS. 9 and 10.

FIGS. 9 through 11 show an optical system provided in a fourth embodiment of the multifocal IOL simulator according to the present invention, i.e., a second embodiment of the corneal effect compensation type of multifocal intraocular lens simulator according to the present invention. The optical system of this multifocal IOL simulator is provided with an afocal optical system (primary afocal optical system) 30, the angular magnification of which is approximately 1 and an IOL optical system 200N positioned at the entrance pupil of the afocal optical system 30. The IOL optical system 200N is provided with an IOL holder 20N and a front optical system (magnifying optical system) 40N positioned in front of the IOL holder 20N. An observer's eye 16 is placed at the exit pupil of the afocal optical system 30. The afocal optical system 30 shown in FIG. 9 is identical to that shown in FIG. 3.

The IOL holder 20N is the same as the IOL holder 20 of the first embodiment shown in FIGS. 1 and 2 except that the IOL holder 20N is provided with a negative lens element 21N and a positive lens element 22P instead of the pair of transparent parallel plates 21 and 22 of the IOL holder 20, respectively. The multifocal IOL 24 and the compensator lens 25 shown in FIGS. 9 through 11 are the same as those shown in FIGS. 1 and 2.

The front optical system 40N consists of a positive lens element 41 and a negative lens element 42, while the optical system of the IOL holder 20N consists of a negative lens element 21N, the compensator lens 25, the multifocal IOL 24 and the positive lens element 22P. The combined angular magnification of the front optical system 40N, and the multifocal IOL 24, the compensator lens 25 and the positive lens element (rear optical system) 22P that are included in the IOL holder 20N is set to approximately 1. Setting the aforementioned combined angular magnification of the IOL optical system 200N, which ranges from the front optical system 40N to the positive lens element 22P, to approximately 1 makes it possible to maintain an appropriate perception of perspective of objects which are seen through the simulator. FIG. 11 shows an embodiment of a test lens holder for the IOL optical system 200N that includes the IOL holder 20N and the front optical system 40N.

The afocal optical system 30 shown in FIG. 9 is provided with two Keplerian afocal optical systems 31 and 32 which are symmetrically arranged. The Keplerian afocal optical system 31, which is positioned toward the IOL holder 20, is provided with a positive lens group 31a, an erecting optical system 31b having a total of four reflecting surfaces, and a positive lens group 31c, in that order from the object side. An image plane (primary image plane) 31p is formed between the positive lens group 31a and the erecting optical system 31b. The Keplerian afocal optical system 32, which is positioned toward the eye 16, is provided with a positive lens group 32a, an erecting optical system 32b having a total of four reflecting surfaces, and a positive lens group 32c, in that order from the Keplerian afocal optical system 31 side. An image plane (secondary image plane) 32p is formed between the erecting optical system 32b and the positive lens group 32c. The positive lens group 31a and the positive lens group 32c are the same and symmetrically arranged, the erecting optical system 31b and the erecting optical system 32b are the same and symmetrically arranged, and the positive lens group 31c and the positive lens group 32a are the same and symmetrically arranged. The two Keplerian afocal optical systems 31 and 32 shown in FIG. 9 are identical to those shown in FIG. 3.

Since the angular magnification of the afocal optical system 30 (i.e., the combined angular magnification of the Keplerian afocal optical system 31 positioned toward the IOL holder 20N and the Keplerian afocal optical system 32 positioned toward the eye 16) and the pupil magnification thereof are each approximately 1, the afocal optical system 30 only has the capability of simply relaying the optical effect of the IOL holder 20N, which includes the multifocal IOL 24 that is positioned at the entrance pupil, to the position of the exit pupil. Namely, unlike the first embodiment of the corneal effect compensation type of multifocal intraocular lens simulator, the afocal optical system 30 is not designed to cancel out the angular magnification of the front optical system 40N that is for simulation of a cornea. Accordingly, in the second embodiment of the corneal effect compensation type of multifocal intraocular lens simulator, the IOL optical system 200N is provided with the optical function, that is undertaken by the afocal optical system 10 in the first embodiment of the corneal effect compensation type of multifocal intraocular lens simulator, for making the relationship between the on-axis light bundle diameter at the multifocal IOL 24 and the diameter of a light bundle on an observer's cornea close to that of a state where the multifocal IOL 24 is actually implanted in an observer's eye. Namely, the optical arrangement of the IOL optical system 200N is such that the front optical system 40N (which includes the negative lens element 21N) of the IOL optical system 200N allows a light bundle which emerges from the multifocal IOL 24 (as a diverging light bundle with a predetermined degree of divergence) and allows this diverging bundle of rays incident on the positive lens element (rear optical system) 22P positioned a predetermined distance apart from the multifocal IOL 24 so that the ratio of the on-axis light bundle diameter of the light bundle which emerges from the positive lens element 22P to the on-axis light bundle diameter of the light bundle which emerges from the multifocal IOL 24 becomes equal to 1/0.89 (=1.12 times). In addition, the positive power of the positive lens element 22P is determined so that the bundle of light which emerges from the positive lens element 22P is collimated to be incident on the afocal optical system 30. The negative lens element 21N functions to convert the light bundle incident on the multifocal IOL 24 into a diverging light bundle. In the present embodiment shown in FIGS. 9 through 11, in the case where a collimated light bundle is made incident on the front optical system 40, the positive lens element 41 and the negative lens element 42 serve as a Galilean afocal system. Accordingly, this Galilean afocal system makes the light bundle incident on the negative lens element 21N become a collimated light bundle, and the on-axis light bundle emerging from the positive lens element (rear optical system) 22P also becomes a collimated light bundle, and accordingly, the IOL holder 20N constitutes an inverted Galilean afocal optical system. In addition, the IOL holder 20N is configured so that the angular magnification of the IOL optical system 200N is maintained to be approximately 1.

As described above, the installation of the front optical system 40N, the collimator lens 25, the multifocal IOL 24 and the position lens element (rear optical system) 22P in the IOL optical system 200N makes it possible to simulate the effect of an observer's cornea with the pupil diameter of the multifocal IOL 24 and the pupil diameter of the crystalline lens being made substantially identical to each other. With this structure, the ratio between the diameter of the on-axis light bundle incident on the negative lens element 21N and the diameter of the on-axis light bundle emerging from the positive lens element 22P becomes greater than the aforementioned ratio (1/0.89 (=1.12 times)) between the diameter of the on-axis light bundle emerging from the multifocal IOL 24 and the diameter of the on-axis light bundle emerging from the positive lens element 22P. In the present embodiment shown in FIGS. 9 through 11, the pupil magnification of the front optical system 40N is 0.78 times (the angular magnification thereof is 1.29 times). Additionally, in the present embodiment shown in FIGS. 9 through 11, the positive lens element 22P is set to be substantially identical in power to a cornea to be used as a quasi-cornea, so that the intraocular IOL 24 is held at a position where the on-axis light bundle diameter is reduced to approximately 0.83 times. With this configuration, also the relationship between the positive lens element 22P, which serves as a quasi-cornea, and the incident/exit angles of the on-axis light bundle on/from the multifocal IOL 24 is set to be close to that of a state in which the multifocal IOL 24 is actually implanted in an eye. Since the IOL holder 20N (Galilean afocal system) is structured so that the angular magnification thereof becomes approximately 1, the angular magnification of the entire optical system shown in FIG. 9 is maintained approximately 1 even if the multifocal IOL 24 is installed at the position of the entrance pupil of the afocal optical system 30.

Numerical Embodiment 4 for the optical system shown in FIG. 9 will be discussed hereinafter.

Numerical Embodiment 4

TABLE 5 below shows lens data in Numerical Embodiment 4 for the optical system shown in FIG. 9. The surface numbers 1 through 6 designate surfaces of the front optical system 40, the surface numbers 7 and 8 designate surfaces of the compensator lens 25, the surface numbers 9 and 10 designate surfaces of the multifocal IOL 24, the surface numbers 11 and 12 designate surfaces of the positive lens element (rear optical system) 22P, the surface numbers 13 through 28 designate surfaces of the Keplerian afocal optical system 31, and the surface numbers 29 through 44 designate surfaces of the Keplerian afocal optical system 32. The Keplerian afocal optical system 31 and the Keplerian afocal optical system 32 are mutually identical, each having an angular magnification of 8 (8×). The compensator lens 25 can be omitted if a test piece with no primary refractive power to which only a differential refractive power is given is used instead of a multifocal IOL. Lens data on the surface numbers 7 through 44 shown in TABLE 5 are identical to lens data on the surface numbers 3 through 40 shown in TABLE 2.

TABLE 5

| NO | R | d | N(d) | ν(d) | |
|---|---|---|---|---|---|
| 1 | 32.000 | 3.500 | 1.77250 | 49.6 | |
| 2 | −73.650 | 4.800 | | | |
| 3 | −36.400 | 1.500 | 1.80100 | 35.0 | |
| 4 | 36.400 | 1.000 | | | |
| 5 | −10.500 | 1.000 | 1.49176 | 57.4 | |
| 6 | 21.500 | 0.930 | 1.33304(water) | 55.8 | |
| 7 | −13.65 | 0.500 | 1.49176 | 57.4 | Compensator Lens |

TABLE 5-continued

| NO | R | d | N(d) | ν(d) | |
|---|---|---|---|---|---|
| 8 | 17.9 | 0.200 | 1.33304(water) | 55.8 | |
| 9 | 17.9 | 1.000 | 1.49176 | 57.4 | IOL (20D) |
| 10 | −13.9 | 1.500 | 1.33304(water) | 55.8 | |
| 11 | ∞ | 2.000 | 1.49176 | 57.4 | |
| 12 | −11.700 | 17.000 | | | |
| 13 | −336.4 | 6.496 | 1.62041 | 60.3 | |
| 14 | −22.388 | 0.232 | | | |
| 15 | 26.448 | 11.600 | 1.62041 | 60.3 | |
| 16 | −21.46 | 2.320 | 1.80518 | 25.5 | |
| 17 | −188.5 | 20.834 | | | |
| 18 | ∞ | 52.850 | 1.51680 | 64.2 | |
| 19 | ∞ | 0.928 | | | |
| 20 | ∞ | 36.285 | 1.56883 | 56.0 | |
| 21 | ∞ | 32.434 | | | |
| 22 | −93.448 | 2.320 | 1.51742 | 52.2 | |
| 23 | 485.008 | 35.102 | | | |
| 24 | ∞ | 5.800 | 1.51680 | 64.2 | |
| 25 | −87.904 | 0.348 | | | |
| 26 | 734.524 | 2.900 | 1.69895 | 30.0 | |
| 27 | 111.558 | 8.120 | 1.51680 | 64.2 | |
| 28 | −111.558 | 16.240 | | | |
| 29 | 111.558 | 8.120 | 1.51680 | 64.2 | |
| 30 | −111.558 | 2.900 | 1.69895 | 30.0 | |
| 31 | −734.524 | 0.348 | | | |
| 32 | 87.904 | 5.800 | 1.51680 | 64.2 | |
| 33 | ∞ | 35.102 | | | |
| 34 | −485.008 | 2.320 | 1.51742 | 52.2 | |
| 35 | 93.448 | 32.434 | | | |
| 36 | ∞ | 36.285 | 1.56883 | 56.0 | |
| 37 | ∞ | 0.928 | | | |
| 38 | ∞ | 52.850 | 1.51680 | 64.2 | |
| 39 | ∞ | 20.834 | | | |
| 40 | 188.5 | 2.320 | 1.80518 | 25.5 | |
| 41 | 21.46 | 11.600 | 1.62041 | 60.3 | |
| 42 | −26.448 | 0.232 | | | |
| 43 | 22.388 | 6.496 | 1.62041 | 60.3 | |
| 44 | 336.4 | 20.000 | | | |

Angular magnification of entire optical system = 1.00
Diameter of on-axis light bundle incident on front optical system φ1 = 6.28
Diameter of on-axis light bundle emerging from front optical system to proceed toward test IOL φ2 = 5.48 φ2/φ1 = 0.87

An index (e.g., a reticle) is positioned at a distance 8.12 mm behind the exit surface (NO. 39) of the erecting optical system 32b (at the image plane 32p). The d value 20 of the surface number 44 designates the distance (eye relief) from the lens surface 44 to an eye point (at which marginal rays intersect the optical axis). In an ideal observing state, the position of the exit pupil of the afocal optical system 30 coincides with this eye point.

Figure 12:
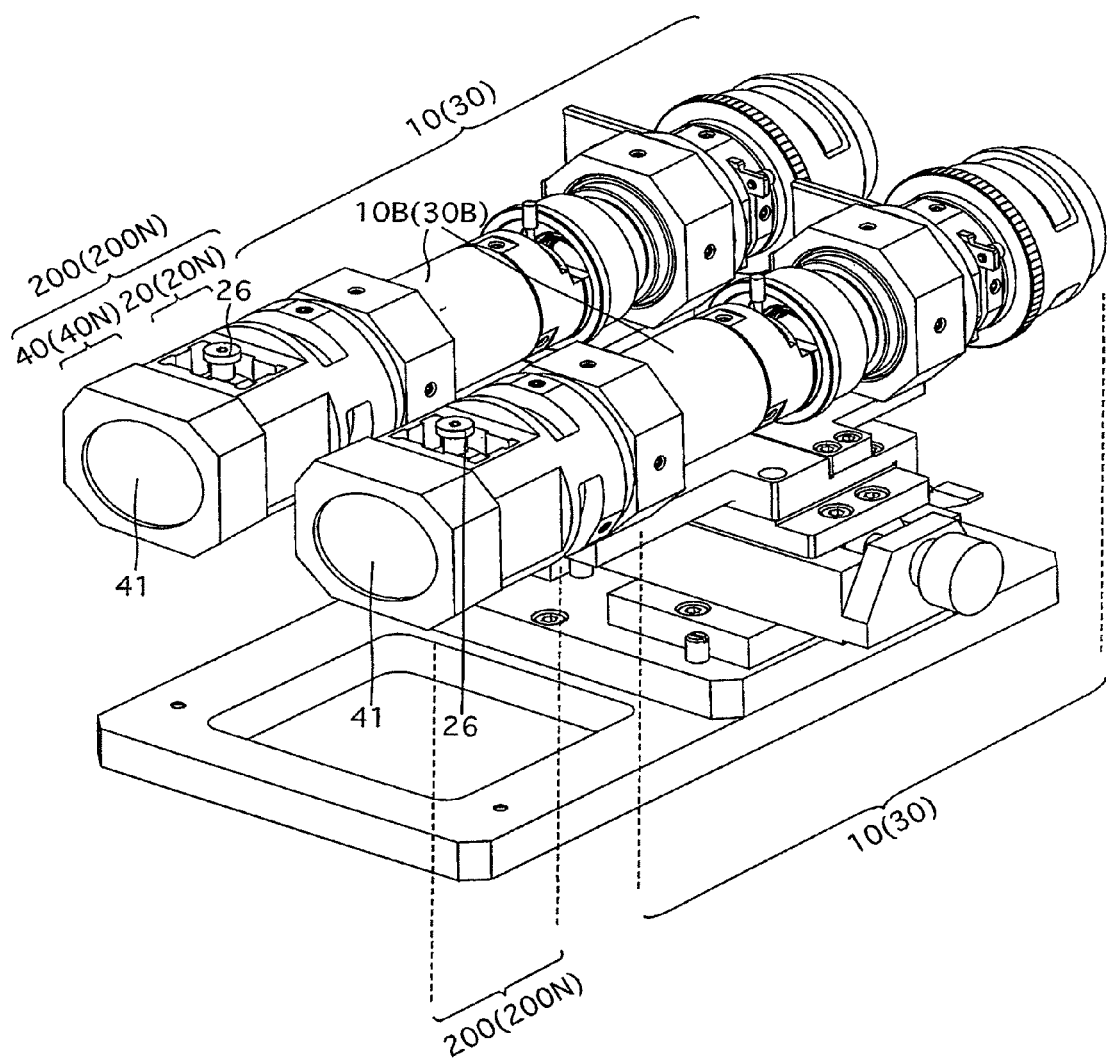
FIG. 12 is a perspective view of an embodiment of the corneal effect compensation type of multifocal intraocular lens simulator according to the present invention in the case where the multifocal intraocular lens simulator is constructed as a binocular type.

FIG. 12 shows an embodiment of the multifocal intraocular lens simulator according to the present invention in the case where the multifocal intraocular lens simulator having the afocal optical system 10 shown in FIG. 6 or the afocal optical system 30 shown in FIG. 9 is constructed as a binocular type. This binocular-type multifocal intraocular lens simulator is provided with a pair of (right and left) optical barrels 10B, each of which contains the afocal optical system 10 shown in FIG. 6, or a pair of optical barrels 30B, each of which contains the afocal optical system 30 shown in FIG. 9. The front ends of the pair of optical barrels 10B or 30B in FIG. 12 are each provided at the front end thereof with the IOL holder 200 shown in FIGS. 7 and 8 or the IOL holder 200N shown in FIGS. 10 and 11. According to this binocular-type multifocal intraocular lens simulator, one can perceive the simulation effect through both eyes (binocular vision).

FIGS. 13 through 20C show an embodiment of a pupil diameter response type of multifocal intraocular lens simulator according to the present invention.

Figure 19B:
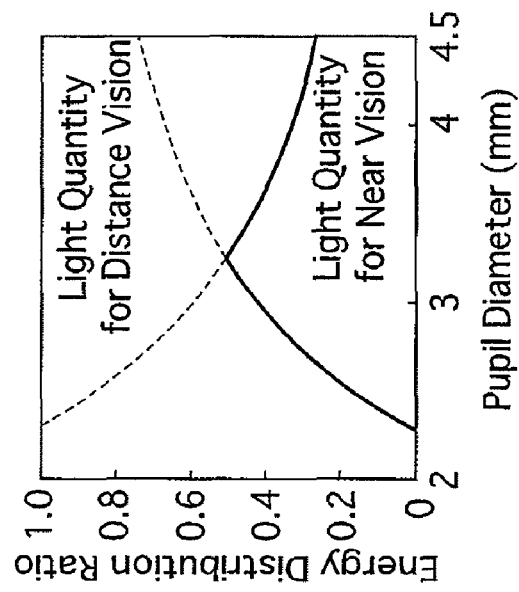
FIG. 19B is a graph showing an example of the energy distribution of light quantity for distance vision and near vision which is incident on a pupil through the intraocular lens shown in FIG. 19A (this graph is also disclosed in the above-mentioned book entitled "MULTIFOCAL IOL" by Hiroko Bissen-Miyajima, published by Elsevier Japan KK)
Figure 19A:
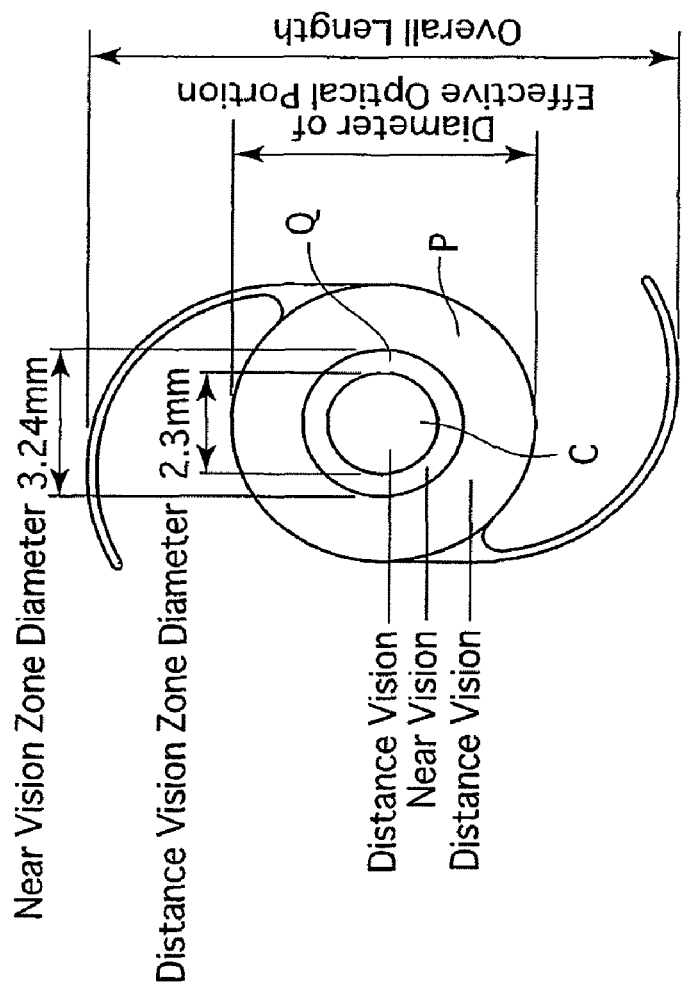
FIG. 19A is a front elevational view of an example of refractive type of multifocal intraocular lens (this drawing is disclosed in a book entitled "MULTIFOCAL IOL" by Hiroko Bissen-Miyajima, published by Elsevier Japan KK)

FIG. 19A shows an example of a refractive type of multifocal IOL. This multifocal IOL is provided with a monofocal central range C for distance vision (first zone for distance vision), a monofocal outermost range P for distance vision and an intermediate range Q for near vision formed between the monofocal central range C and the monofocal outermost range P. FIG. 19B shows an example of the energy distribution of light quantity for distance vision and near vision which is incident on a pupil through the intraocular lens shown in FIG. 19A. Upon the diameter (pupil diameter) reaching a predetermined value, only the energy for distance vision which is focused at far distance (infinite distance) through the monofocal central range C is incident on the pupil. When the pupil diameter reaches the intermediate range Q, the energy for near vision which is focused at near distance (finite distance) increases while the energy for distance vision which is focused at far distance (infinite distance) decreases. When the pupil diameter reaches the monofocal outermost range P, the energy for distance vision which is focused at far distance (infinite distance) increases while the energy for near vision which is focused at near distance (finite distance) decreases. This optical design is based on the idea that only the energy for distance vision which is focused at far distance is given while the pupil diameter is quite small, that the energy for distance vision which is focused at far distance and the energy for near vision which is focused at near distance are decreased and increased, respectively, as the pupil diameter increases, and that the energy for distance vision which is focused at far distance is again increased when the pupil diameter further increases.

Figure 20A:
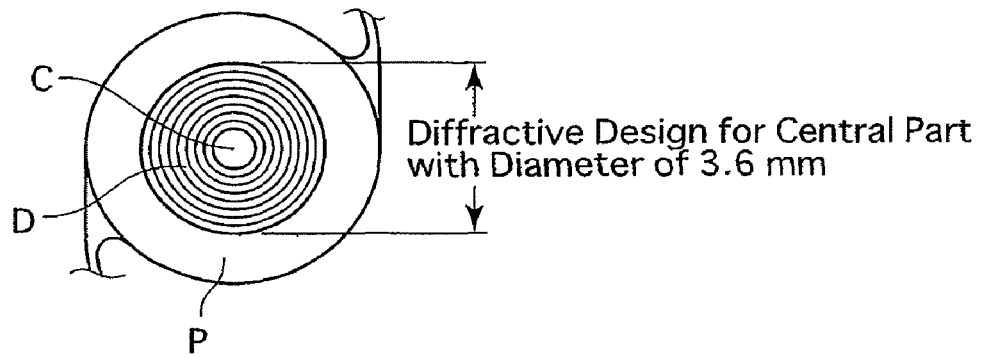
FIG. 20A is a front elevational view, partly omitted, of an example of a diffractive type of multifocal intraocular lens.
Figure 20B:
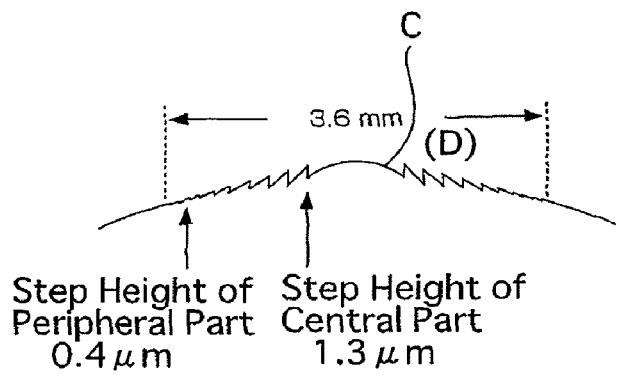
FIG. 20B is a cross sectional view of a surface of the intraocular lens shown in FIG. 20A which has a diffraction grating.
Figure 20C:
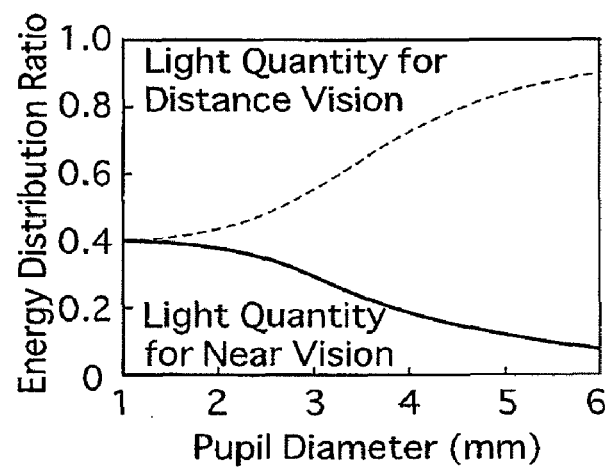
FIG. 20C is a graph showing the energy distribution of light quantity for distance vision and near vision which is incident on the pupil through the intraocular lens shown in FIG. 20A.

FIG. 20A is a front elevational view, partly omitted, of an example of diffractive type of multifocal IOL. This multifocal IOL is provided with a monofocal outermost range P for distance vision and a central near-far transitional range D having a diffractive structure formed on a central portion of the IOL. FIG. 20B shows a cross sectional view of the central near-far transitional range D, showing the diffractive structure thereof. The central near-far transitional range D is shaped to gradually decrease the step heights of the diffraction gratings radially outwards from a central portion C to thereby be given an apodization effect. FIG. 20C shows the energy distribution of light quantity for distance vision and near vision which is incident on the pupil through the multifocal IOL shown in FIG. 20A. As shown in FIG. 20C, the energy for distance vision which is focused at far distance (infinite distance) smoothly increases and the energy for near vision which is focused at near distance (finite distance) smoothly decreases as the diameter (pupil diameter) increases. This optical design is based on the idea that the energy for near vision which is focused at near distance is made greater than the energy for distance vision which is focused at far distance while the pupil diameter is small, and the energy for far vision which is focused at far distance is made greater than the energy for near vision which is focused at near distance as the pupil diameter increases.

As is apparent from the above described two examples of multifocal IOLs, the energy distribution of light quantity for distance vision and near vision varies depending on the lens type, so that the optical performance of a multifocal IOL cannot be evaluated properly without consideration given to the pupil diameter.

Fifth Embodiment

Figure 13:
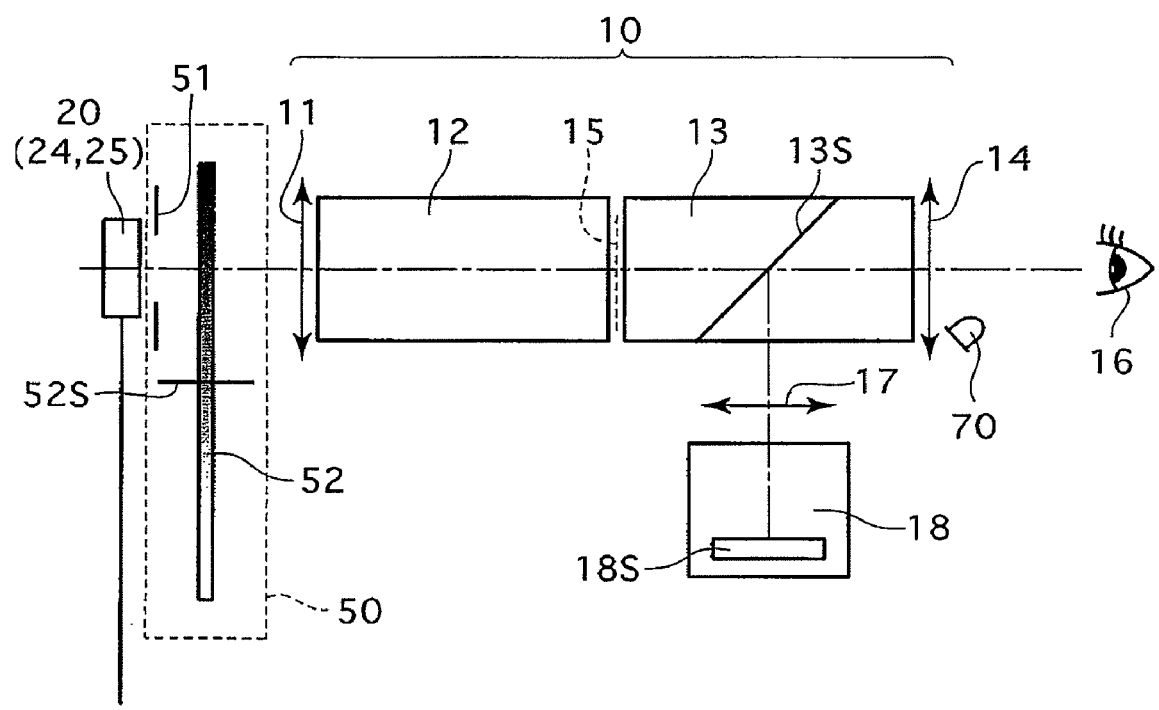
FIG. 13 is a diagrammatic sketch showing an optical configuration of a first embodiment of a pupil diameter response type of multifocal intraocular lens simulator according to the present invention.
Figure 14:
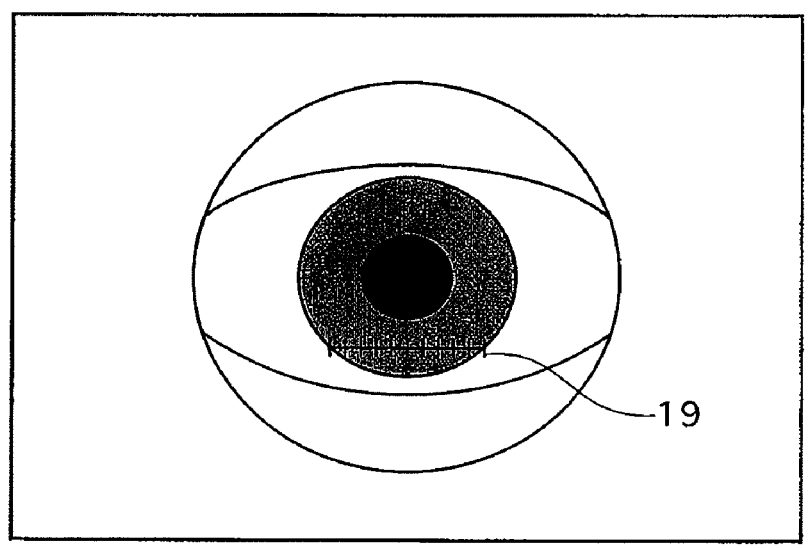
FIG. 14 is a schematic diagram showing an image which is captured by an imaging apparatus (shown in FIG. 13) and displayed on a display monitor.

FIGS. 13 and 14 show a fifth embodiment of the multifocal IOL simulator according to the present invention, specifically a first embodiment of a pupil diameter response type of multifocal intraocular lens simulator according to the present invention. This multifocal IOL simulator is provided with an afocal optical system 10, the angular magnification of which is approximately 1 and an IOL holder (test lens holder) 20 positioned at the entrance pupil of the afocal optical system 10. The afocal optical system 10 is designed such that parallel rays (rays from an infinite object) entering the afocal optical system 10 are also substantially parallel when they exit.

The afocal optical system 10 is provided with an objective lens group 11 having positive power, a first prism 12, a second prism 13 and an eyepiece lens group 14 having positive power, in that order from the object side. An image plane 15 is formed between the first prism 12 and the second prism 13. Further descriptions of the afocal optical system 10 shown in FIG. 13 are omitted since the afocal optical system 10 shown in FIG. 13 is substantially the same as that described with reference to FIG. 1.

The second prism 13 is provided therein with a beam splitting surf ace (coating) 13S serving as a beam splitter which is angled relative to the optical axis at an angle of 45 degrees. The incident light on the beam splitting surface 13S from the eye 16 is partly reflected by the beam splitting surface 13S to proceed toward the outside of the afocal optical system 10 (downward with respect to FIG. 13) through a branch optical path on which an imaging lens 17 and an imaging apparatus 18 containing an image sensor 18S are arranged, so that the light bundle which is reflected by the beam splitting surface 13S to proceed toward the imaging apparatus 18 passes through the imaging lens 17 and is thereafter incident on the image sensor 18S. Accordingly, the beam splitting surface 13S, the imaging lens 17 and the imaging apparatus 18 constitute an optical system for observing the pupil diameter of the eye 16. FIG. 14 is a schematic diagram showing an image which is captured by the imaging apparatus 18. An index 19 for measurement of the pupil diameter is provided in a viewing field in the close vicinity of the real image formed in the afocal optical system 10.

The IOL holder 20 shown in FIG. 13 is identical to that described with reference to FIG. 21, so that the IOL holder 20 holds a multifocal IOL 24 and a compensator lens 25 therein as shown in FIG. 2. As described above, the IOL holder 20 is positioned so that the multifocal IOL 24 is positioned at the entrance pupil of the afocal optical system 10. Regardless of as to whether the multifocal IOL 24 is of refractive type or diffractive type, the multifocal IOL 24 has a primary refractive power (e.g., 20D) for use in water (as a substitution of crystalline lens) and an additional refractive power (e.g., 24D) which corresponds to the primary refractive power to which a differential refractive power is added, and an example of the energy distribution therefor has been discussed above with reference to FIGS. 19 and 20. The compensator lens 25 has a negative refractive power which compensates for the primary refractive power of the multifocal IOL 24 to extract only a difference (4D) between the primary refractive power and the additional refractive power.

A light quantity controller 50 is installed between the afocal optical system 10 and the IOL holder 20. The light quantity controller 50 includes an adjustable diaphragm apparatus 51 and a rotational ND filter 52. The adjustable diaphragm apparatus 51 operates to vary the diameter of a mechanical aperture thereof to vary (increase/decrease) the amount of light incident on the afocal optical system 10. The rotational ND filter 52 is rotatable about a rotational shaft 52S and changes the light transmittance (density) in the circumferential direction about the rotational shaft 52S continuously or stepwise. By rotating the rotational ND filter 52 about the rotational shaft 52S to change the portion of the rotational ND filter 52 on the optical axis, the amount of light incident on the afocal optical system 10 can be varied as with the adjustable diaphragm apparatus 51.

According to the above described pupil diameter response type of multifocal intraocular lens simulator shown in FIG. 13, an observer can observe objects through the multifocal IOL 24 and the afocal optical system 10, which are installed in the IOL holder 20, from the rear of the afocal optical system 10. Accordingly, the position of the exit pupil of the afocal optical system is opened to allow an observer's eye to be placed thereat. In addition, the IOL holder 20 (the multifocal IOL 24) is installed at a position (pupil conjugate point) optically conjugate with the position where an eye (pupil) of the observer is to be placed, and accordingly, the optical effect of the multifocal IOL 24 of the IOL holder 20 positioned in front of the afocal optical system 10 can be relayed to the observer's eye 16 (a vicinity of the crystalline lens thereof) that is placed behind the afocal optical system 10, which makes it possible to have the observer perceive visibility similar to what he or she would actually perceive when wearing the multifocal IOL 24. The angular magnification of the afocal optical system 10 is 1, so that one can see objects (external scenery, objects, etc.) through the optical system of the multifocal intraocular lens simulator at the same magnification as the naked eye. It is desirable that the diameter of the entrance pupil of the afocal optical system 10 be greater than the diameter of the multifocal IOL 24.

By making the observer gaze steadily at an index (e.g., a reticle) installed (e.g., printed, engraved or embedded) in the vicinity of the image plane 15, the reticle functions to reduce the accommodation action of the eye to a minimum, thus making it easier for the observer to perceive the differential refractive power.

The pupil diameter of the eye 16 of the observer looking into the above described pupil diameter response type of multifocal intraocular lens simulator shown in FIG. 13 can be observed via the imaging lens 17 and the imaging apparatus (pupil diameter observing optical system) 18, thus being capable of being directly read with the index 19. Accordingly, the multifocal IOL 24 can be evaluated in consideration of both the pupil diameter and an example of the energy distribution shown in FIG. 19A or 20C. Additionally, the pupil diameter of the eye 16 of an observer can be decreased and increased by increasing and decreasing the amount of light incident on the eye 16 through the use of one or both of the adjustable diaphragm apparatus 51 and the rotational ND filter 52 of the light quantity controller 50, so that one can actually perceive visibility similar to what he or she would actually perceive when wearing the multifocal IOL 24.

Sixth Embodiment

Figure 15:
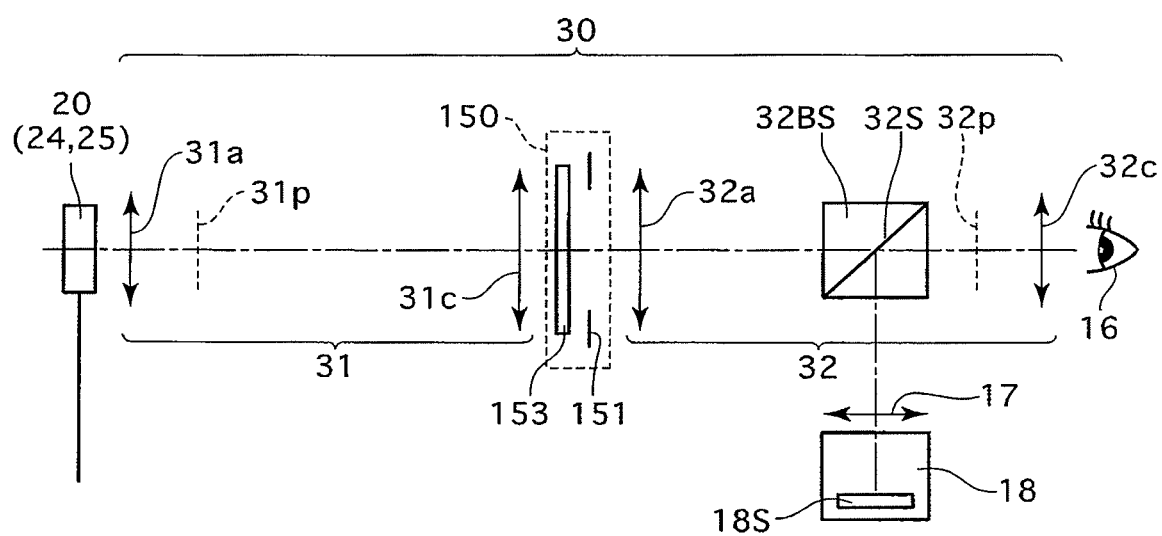
FIG. 15 is an optical diagram of an optical system provided in a second embodiment of the pupil diameter response type of multifocal intraocular lens simulator according to the present invention.

FIG. 15 shows a sixth embodiment of the multifocal IOL simulator according to the present invention, i.e., a second embodiment of the pupil diameter response type of multifocal intraocular lens simulator according to the present invention. This multifocal IOL simulator is provided with an afocal optical system 30, the angular magnification of which is approximately 1, and an IOL holder (test lens holder) 20 positioned at the entrance pupil of the afocal optical system 30. An observer's eye 16 is placed at the exit pupil of the afocal optical system 30. The IOL holder 20 in this embodiment is identical to that in the first embodiment of the multifocal IOL simulator shown in FIG. 2.

The afocal optical system 30 shown in FIG. 15 is identical to that shown in FIG. 3 except that the afocal optical system 30 shown in FIG. 15 is further provided with a beam splitter 32BS. Note that erecting optical systems 31b and 32b shown in FIG. 3 are not shown in FIG. 15. As described above, the afocal optical system 30 is provided with two Keplerian afocal optical systems 31 and 32 which are symmetrically arranged. The Keplerian afocal optical system 31, which is positioned toward the IOL holder 20, is provided with a positive lens group 31a and a positive lens group 31c in that order from the object side. An image plane (primary image plane) 31p is formed between the positive lens group 31a and the positive lens group 31c. The Keplerian afocal optical system 32, which is positioned toward the eye 16, is provided with a positive lens group 32a and a positive lens group 32c, in that order from the Keplerian afocal optical system 31 side. An image plane (secondary image plane) 32p is formed between the positive lens group 32a and the positive lens group 32c. The positive lens group 31a and the positive lens group 32c are the same and symmetrically arranged, and the positive lens group 31c and the positive lens group 32a are the same and symmetrically arranged. In the afocal optical system 30 shown in FIG. 15, the positive lens group 31c of the Keplerian afocal optical system 31 and the positive lens group 32a of the Keplerian afocal optical system 32 that face each other function as a relay optical system and constitute a Keplerian optical system the angular magnification of which is approximately 1.

The Keplerian afocal optical system 32 is provided therein with the aforementioned beam splitter 32BS that includes a beam splitting surface 32S identical in function to the beam splitting surface 13S shown in FIG. 13. The incident light on the beam splitting surface 32S from the eye 16 is partly reflected by the beam splitting surface 32S to proceed toward the outside of the afocal optical system 10 through a branch optical path on which an imaging lens 17 and an imaging apparatus 18 containing an image sensor 18S (which are identical to those in the embodiment shown in FIG. 13) are arranged. Accordingly, the pupil diameter of the eye 16 can be observed through a pupil diameter observing optical system consisting of the imaging lens 17 and the imaging apparatus 18.

In addition, a light quantity controller 150 is installed between the positive lens groups 31c of the Keplerian afocal optical system 31 and the positive lens group 32a of the Keplerian afocal optical system 32. The light quantity controller 150 includes an adjustable diaphragm apparatus 151 and an insertion/removal type ND filter 153 provided instead of the rotational ND filter 52 shown in FIG. 13.

In the above described second embodiment of the pupil diameter response type of multifocal intraocular lens simulator also, an observer can observe objects through the multifocal IOL 24 in the IOL holder 20 and the afocal optical system 30 from the rear thereof. Namely, the position of the exit pupil of the afocal optical system 30 is opened to allow an eye of the observer to be positioned thereat. In addition, the IOL holder 20 (the multifocal IOL 24) is installed at a position (pupil conjugate point) optically conjugate with the position where an eye (pupil) of the observer is to be placed, and accordingly, the optical effect of the multifocal IOL 24 of the IOL holder 20 positioned in front of the afocal optical system 30 can be relayed to the observer's eye 16 (at or at a close vicinity of the crystalline lens thereof) that is placed behind the afocal optical system 30 via the positive lens group 31c and the positive lens group 32a, which makes it possible to have the observer perceive visibility similar to what he or she would actually perceive when wearing the multifocal IOL 24. The angular magnification of the afocal optical system 30 is 1, so that one can see objects (external scenery, objects, etc.) through the optical system of the multifocal intraocular lens simulator at the same magnification as the naked eye. It is desirable that the diameter of the entrance pupil of the afocal optical system 30 be greater than the diameter of the multifocal IOL 24.

Additionally, similar to the above described first embodiment of the pupil diameter response type of multifocal intraocular lens simulator, the pupil diameter of the eye 16 of the observer looking into the second embodiment of the pupil diameter response type of multifocal intraocular lens simulator shown in FIG. 15 can be observed via the beam splitter 32BS, the imaging lens 17 and the imaging apparatus 18, thus being capable of being directly read with the index 19. Accordingly, the multifocal IOL 24 can be evaluated in consideration of both the pupil diameter and an example of the energy distribution shown in FIG. 19A or 20C. Additionally, the pupil diameter of the eye 16 of an observer can be decreased and increased by increasing and decreasing the amount of light incident on the eye 16 through the use of one or both of the adjustable diaphragm apparatus 51 and the insertion/removal type ND filter 53 of the light quantity controller 150, so that one can actually perceive visibility similar to what he or she would actually perceive when wearing the multifocal IOL 24.

Numerical Embodiment 5 for the optical system shown in FIG. 13 will be discussed hereinafter.

Numerical Embodiment 5

Figure 16:
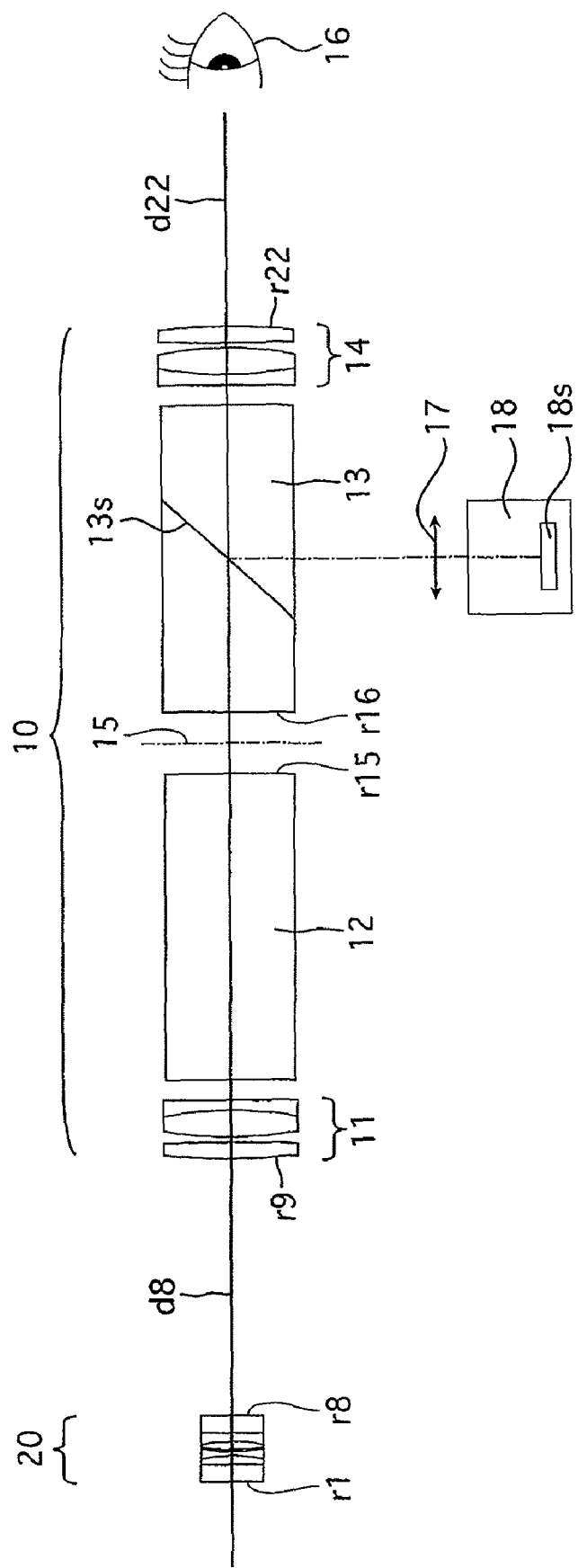
FIG. 16 is an optical diagram of the optical elements provided in the first embodiment of the pupil diameter response type of multifocal intraocular lens simulator shown in FIG. 13, wherein the rotational ND filter shown in FIG. 13 is not shown in this drawing.
Figure 18:
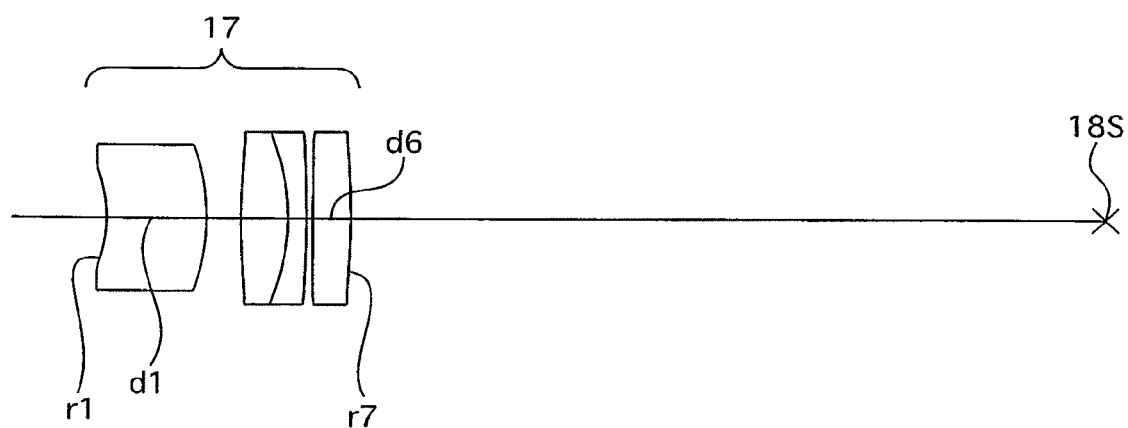
FIG. 18 is a cross sectional view showing an optical configuration of an embodiment of the imaging lens used in each of the first and second embodiments of the pupil diameter response type of multifocal intraocular lens simulator.

TABLE 6 below shows lens data in Numerical Embodiment 5 for the optical system shown in FIG. 13. FIG. 16 shows the optical elements shown in FIG. 13 except the rotational ND filter 52. Lens data shown in TABLE 6 is identical to that shown in TABLE 1. The beam splitting surface (coating) 13S is formed inside the prism 13. FIG. 18 shows an optical configuration of an embodiment of the imaging lens 17 and TABLE 7 shows lens data on this embodiment of the imaging lens 17. Surface numbers 1 through 7 in TABLE 7 designate surfaces of the imaging lens 17 from the prism 13 side.

TABLE 6

| NO | R | d | N (d) | ν (d) |
|---|---|---|---|---|
| 1 | ∞ | 2.000 | 1.51633 | 64.1 |
| 2 | ∞ | 1.000 | 1.33304 (water) | 55.8 |
| 3 | −13.650 | 0.500 | 1.49176 | 57.4 (compensator lens) |
| 4 | 17.900 | 0.200 | 1.33304 (water) | 55.8 |
| 5 | 17.900 | 1.000 | 1.49176 | 57.4 (IOL(20D)) |
| 6 | −13.9 | 1.000 | 1.33304 (water) | 55.8 |
| 7 | ∞ | 2.000 | 1.51633 | 64.1 |
| 8 | ∞ | 30.000 | | |
| 9 | 61.392 | 1.920 | 1.69680 | 55.5 |
| 10 | −205.560 | 0.600 | | |
| 11 | 37.320 | 3.120 | 1.74400 | 44.9 |
| 12 | −37.320 | 1.200 | 1.84666 | 23.8 |
| 13 | 480.000 | 2.400 | | |
| 14 | ∞ | 36.000 | 1.51633 | 64.1 (prism) |
| 15 | ∞ | 7.300 | | |
| 16 | ∞ | 36.000 | 1.51633 | 64.1 (prism) |
| 17 | ∞ | 2.400 | | |
| 18 | −480.000 | 1.200 | 1.84666 | 23.8 |
| 19 | 37.320 | 3.120 | 1.74400 | 44.9 |
| 20 | −37.320 | 0.600 | | |
| 21 | 205.560 | 1.920 | 1.6968 | 55.5 |
| 22 | −61.392 | 34.000 | | |

Angular magnification of entire optical system = 0.99

TABLE 7

| No. | R | d | N (d) | ν (d) | N (850 nm) |
|---|---|---|---|---|---|
| 1 | −4.743 | 2.700 | 1.84666 | 23.8 | 1.82037 |
| 2 | −5.997 | 0.900 | | | |
| 3 | 32.385 | 1.200 | 1.61800 | 63.4 | 1.60987 |
| 4 | −7.140 | 0.500 | 1.80518 | 25.4 | 1.78162 |
| 5 | −30.622 | 0.150 | | | |
| 6 | 136.146 | 1.000 | 1.75500 | 52.3 | 1.74299 |
| 7 | −31.019 | 20.185 | | | |

The reason why the refractive index at a wavelength of 850 nm is included with lens data in TABLE 7 is because it is desirable that an infrared LED illumination 70 (see FIG. 13) be installed behind the eyepiece lens group 14 between the eyepiece lens group 14 and the eye 16 in order to illuminate the eye 16 without exerting influence on the operation of the first embodiment of the pupil diameter response type of multifocal intraocular lens simulator.

Numerical Embodiment 6 for the optical system shown in FIG. 15 will be discussed hereinafter.

Numerical Embodiment 6

Figure 17:
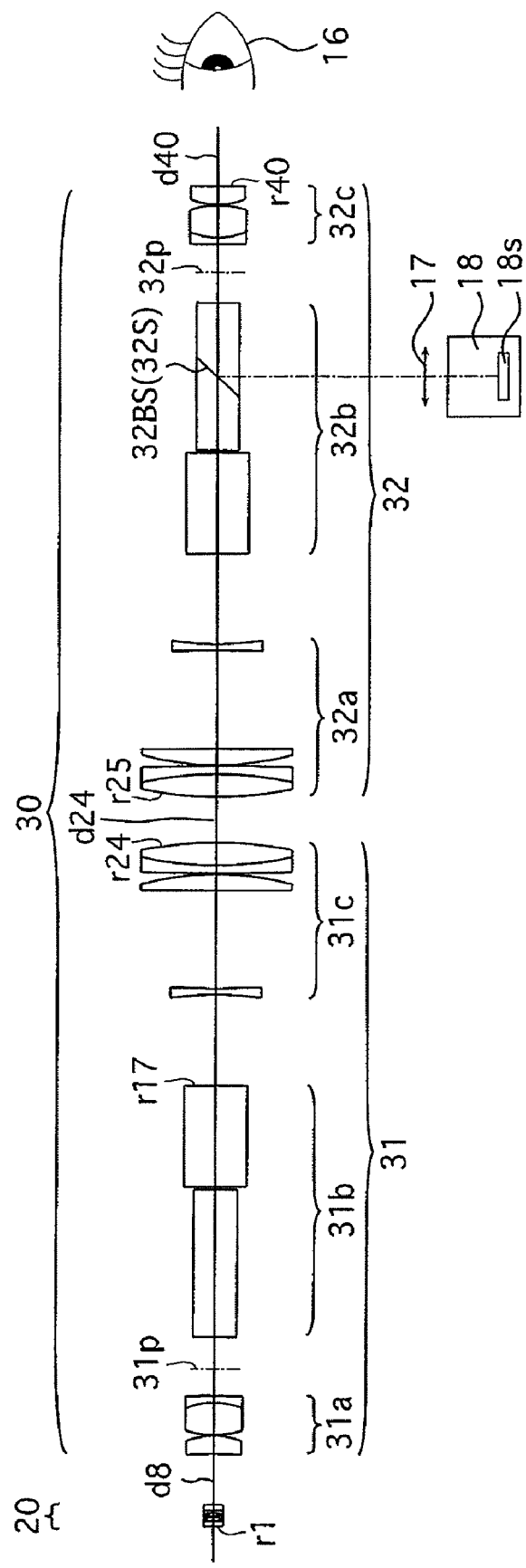
FIG. 17 is an optical path diagram showing an optical system provided in the second embodiment of the pupil diameter response type of multifocal intraocular lens simulator shown in FIG. 15, wherein the insertion/removal ND filter shown in FIG. 15 is not shown in this drawing.

TABLE 8 below shows lens data in Numerical Embodiment 6 for the optical system shown in FIG. 15. FIG. 17 shows the optical elements shown in FIG. 15 except the insertion/removal ND filter 53. Lens data shown in TABLE 8 is identical to that shown in TABLE 2. The beam splitter 32BS (the beam splitting surface 32S) is integrated into a prism provided in the Keplerian afocal optical system 32. The imaging lens 17 shown in FIG. 17 is the same as that shown in FIG. 18 and TABLE 7.

TABLE 8

| NO | R | d | N (d) | ν (d) |
|---|---|---|---|---|
| 1 | ∞ | 2.000 | 1.51633 | 64.1 |
| 2 | ∞ | 1.000 | 1.33304 (water) | 55.8 |
| 3 | −13.650 | 0.500 | 1.49176 | 57.4 (compensator lens) |
| 4 | 17.900 | 0.200 | 1.33304 (water) | 55.8 |
| 5 | 17.900 | 1.000 | 1.49176 | 57.4 (IOL(20D)) |
| 6 | −13.900 | 1.000 | 1.33304 (water) | 55.8 |
| 7 | ∞ | 2.000 | 1.51633 | 64.1 |
| 8 | ∞ | 18.000 | | |
| 9 | −336.400 | 6.496 | 1.62041 | 60.3 |
| 10 | −22.388 | 0.232 | | |
| 11 | 26.448 | 11.600 | 1.62041 | 60.3 |
| 12 | −21.460 | 2.320 | 1.80518 | 25.5 |
| 13 | −188.500 | 20.834 | | |
| 14 | ∞ | 52.850 | 1.51680 | 64.2 |
| 15 | ∞ | 0.928 | | |
| 16 | ∞ | 36.285 | 1.56883 | 56.0 |
| 17 | ∞ | 32.434 | | |
| 18 | −93.448 | 2.320 | 1.51742 | 52.2 |
| 19 | 485.008 | 35.102 | | |
| 20 | ∞ | 5.800 | 1.51680 | 64.2 |
| 21 | −87.904 | 0.348 | | |
| 22 | 734.524 | 2.900 | 1.69895 | 30.0 |
| 23 | 111.558 | 8.120 | 1.51680 | 64.2 |
| 24 | −111.558 | 16.240 | | |
| 25 | 111.558 | 8.120 | 1.51680 | 64.2 |
| 26 | −111.558 | 2.900 | 1.69895 | 30.0 |
| 27 | −734.524 | 0.348 | | |
| 28 | 87.904 | 5.800 | 1.51680 | 64.2 |
| 29 | ∞ | 35.102 | | |
| 30 | −485.008 | 2.320 | 1.51742 | 52.2 |
| 31 | 93.448 | 32.434 | | |
| 32 | ∞ | 36.285 | 1.56883 | 56.0 |
| 33 | ∞ | 0.928 | | |
| 34 | ∞ | 52.850 | 1.51680 | 64.2 |
| 35 | ∞ | 20.834 | | |
| 36 | 188.500 | 2.320 | 1.80518 | 25.5 |

TABLE 8-continued

| NO | R | d | N (d) | ν (d) |
|----|---|---|-------|-------|
| 37 | 21.460 | 11.600 | 1.62041 | 60.3 |
| 38 | −26.448 | 0.232 | | |
| 39 | 22.388 | 6.496 | 1.62041 | 60.3 |
| 40 | 336.400 | 20.000 | | |

Angular magnification of entire optical system = 0.99

Although a simulation of the performance of the multifocal IOL 24 has been discussed above in each of the corneal effect compensation type multifocal intraocular lens simulators shown in FIGS. 6 through 12 and the pupil diameter response type of multifocal intraocular lens simulators shown in FIGS. 13 through 20, a similar simulation can be performed with a test piece optically equivalent to the multifocal IOL 24 as described above with reference to FIG. 4.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A multifocal intraocular lens simulator comprising:
an optical system enabling an object to be observed therethrough; and
a test lens holder which holds a test intraocular lens,
wherein said test lens holder is positioned such that said test intraocular lens is located at a position that is optically conjugate with a position at which an eye of an observer is to be placed to observe the object through the test intraocular lens and through the optical system.

2. A multifocal intraocular lens simulator comprising:
an afocal optical system, wherein a parallel light bundle that enters said afocal optical system is also substantially parallel when emerging from the afocal optical system; and
a test lens holder which holds a test intraocular lens and is positioned in front of said afocal optical system,
wherein an observer can observe an object from the rear of said afocal optical system through said test intraocular lens and said afocal optical system, and
wherein said test lens holder is positioned such that said test intraocular lens is located at a position that is optically conjugate with a position at which an eye of said observer is to be placed.

3. The multifocal intraocular lens simulator according to claim 2, further comprising a front optical system,
wherein said front optical system reduces an on-axis light bundle diameter of a light bundle that is incident on said front optical system before transmitting said light bundle toward said test intraocular lens that is held by said test lens holder,
wherein said front optical system and said test lens holder are positioned in front of said afocal optical system so that said observer can observe the object from the rear of said afocal optical system through said test intraocular lens and said afocal optical system,
wherein a combined angular magnification of an entire optical system that includes said front optical system and said afocal optical system is approximately 1 with said test lens holder holding said test intraocular lens, and
wherein the following condition is satisfied:

$$0.77 < \phi 2/\phi 1 < 0.89$$

wherein φ1 designates the on-axis light bundle diameter of the light bundle that is incident on said front optical system, and
φ2 designates an on-axis light bundle diameter of the light bundle which exits from said front optical system to be incident on said test intraocular lens.

4. The multifocal intraocular lens simulator according to claim 3, wherein said front optical system comprises a magnifying afocal optical system with an angular magnification of approximately 1.2, and
wherein said afocal optical system has an angular magnification of approximately 0.83.

5. The multifocal intraocular lens simulator according to claim 3, further comprising a rear optical system having positive refractive power and that is positioned between said test intraocular lens held by said test lens holder and said afocal optical system,
wherein said front optical system has negative refractive power,
wherein said test intraocular lens is held in a liquid by said test lens holder, and
wherein a combined angular magnification of an optical system ranging from said front optical system to said rear optical system is approximately 1 with said test lens holder holding said test intraocular lens in said liquid.

6. The multifocal intraocular lens simulator according to claim 2, further comprising a light quantity controller positioned along an optical path extending from said test intraocular lens to afocal optical system.

7. The multifocal intraocular lens simulator according to claim 6, wherein said light quantity controller comprises an ND filter.

8. The multifocal intraocular lens simulator according to claim 7, wherein said ND filter is movable so that the light transmittance is one of continuously changed and stepwise changed.

9. The multifocal intraocular lens simulator according to claim 6, wherein said light quantity controller comprises a diaphragm which limits a diameter of a light bundle incident on the eye of the observer.

10. The multifocal intraocular lens simulator according to claim 9, wherein said diaphragm is an adjustable diaphragm which can vary a size of an aperture thereof.

11. The multifocal intraocular lens simulator according to claim 2, further comprising an optical path splitter positioned in an optical path of said afocal optical system to allow a pupil diameter of the observer to be observed through a branch optical path different from said optical path of said afocal optical system.

12. The multifocal intraocular lens simulator according to claim 11, further comprising an image sensor and an imaging lens which are positioned in said branch optical path to capture an image of the pupil.

13. The multifocal intraocular lens simulator according to claim 11, further comprising an index, positioned in said optical path splitter, for measurement of said pupil diameter.

14. The multifocal intraocular lens simulator according to claim 11, further comprising a light quantity controller positioned in an optical path extending from said test intraocular lens to said optical path splitter.

15. The multifocal intraocular lens simulator according to claim 14, wherein said light quantity controller comprises an ND filter.

16. The multifocal intraocular lens simulator according to claim 15, wherein said ND filter is movable so that the light transmittance is one of continuously changed and stepwise changed.

17. The multifocal intraocular lens simulator according to claim 14, wherein said light quantity controller comprises a diaphragm which limits a diameter of a light bundle incident on the eye of the observer.

18. The multifocal intraocular lens simulator according to claim 17, wherein said diaphragm is an adjustable diaphragm which can vary a size of an aperture thereof.

19. The multifocal intraocular lens simulator according to claim 2, wherein said afocal optical system is of Keplerian type, in which a real image of the object is formed in said afocal optical system.

20. The multifocal intraocular lens simulator according to claim 19, wherein said multifocal intraocular lens simulator is of a binocular type having a pair of identical optical systems, said afocal optical system comprising an afocal optical system in each of the pair of identical optical systems.

21. The multifocal intraocular lens simulator according to claim 19, further comprising an index which is provided in a close vicinity of said real image formed in said afocal optical system to indicate a spacial position in the close vicinity of said real image.

22. The multifocal intraocular lens simulator according to claim 19, wherein an angular magnification of said afocal optical system is approximately 1.

23. The multifocal intraocular lens simulator according to claim 22, wherein said afocal optical system comprises two afocal optical systems which are substantially identical in magnifying power and positioned to face each other.

24. The multifocal intraocular lens simulator according to claim 23, wherein said pair of identical optical systems, each of which is provided with one of said pair of two afocal optical systems, comprise a pair of binoculars, and
wherein said test lens holder comprises a pair of test lens holders that correspond to said pair of identical optical systems, respectively.

25. The multifocal intraocular lens simulator according to claim 19, further comprising an adjustable diaphragm installed in said afocal optical system.

26. The multifocal intraocular lens simulator according to claim 1, wherein said test intraocular lens comprises a multifocal intraocular lens which can be implanted in an eye as a substitute for a crystalline lens.

27. The multifocal intraocular lens simulator according to claim 19, wherein said test intraocular lens which is interchangeably held by said test lens holder is one of a refractive-type test piece and a diffractive-type test piece,
wherein, when said test intraocular lens is said refractive-type test piece, one of the following first and second conditions is satisfied:
the first condition is that a primary refractive power of said test intraocular lens that is held by said test lens holder is substantially zero, and
the second condition is that one of a first refractive power and a second refractive power of said test intraocular lens is zero while the other of said first refractive power and said second refractive power has a refractive portion having a differential refractive power.

28. The multifocal intraocular lens simulator according to claim 2, wherein said test intraocular lens is a multifocal intraocular lens provided with a primary refractive power and an additional refractive power, said additional refractive power corresponding to said primary refractive power to which a differential refractive power is added,
wherein said multifocal intraocular lens that is held by said test lens holder is one of a refractive-type test piece and a diffractive-type test piece, and
wherein, when said test intraocular lens is said refractive-type test piece, one of said primary refractive power and said additional refractive power is substantially zero.

29. The multifocal intraocular lens simulator according to claim 26, wherein said test lens holder comprises a liquid holding portion which holds a liquid, and
wherein said multifocal intraocular lens and a compensator lens, which compensates for said primary refractive power of said multifocal intraocular lens, are held in said liquid holding portion filled with said liquid.

30. A method of simulating a multifocal intraocular lens, comprising:
preparing an afocal optical system, wherein a parallel light bundle entering the afocal optical system is also substantially parallel when emerging therefrom;
installing a test intraocular lens in front of the afocal optical system; and
placing an eye of an observer at a position of an exit pupil of the afocal optical system to allow the observer to observe an object through the test intraocular lens and the afocal optical system.

31. A method of simulating a multifocal intraocular lens, comprising:
preparing an afocal optical system, wherein a parallel light bundle entering the afocal optical system is also substantially parallel when emerging therefrom;
installing a front optical system and a test intraocular lens in front of the afocal optical system, the front optical system reducing an on-axis light bundle diameter of a light bundle incident on the front optical system before transmitting the light bundle toward the test intraocular lens; and
placing an eye of an observer at a position of an exit pupil of the afocal optical system to allow the observer to observe an object through the front optical system, the test intraocular lens and the afocal optical system,
wherein a combined angular magnification of an entire optical system that includes the front optical system and the afocal optical system is approximately 1.

* * * * *